US012758387B2

(12) United States Patent
Mousavi

(10) Patent No.: US 12,758,387 B2
(45) Date of Patent: Oct. 13, 2026

(54) SMART PLATFORM BIOPRINTING BED WITH AT LEAST ONE CONTROLLABLE STIMULATOR

(71) Applicant: MOC BIO TECHNOLOGIES INC., Dartmouth (CA)

(72) Inventor: Sayedali Mousavi, Halifax (CA)

(73) Assignee: MOC Bio Technologies Inc., Winnipeg (CA)

( * ) Notice: Subject to any disclaimer, the term of this patent is extended or adjusted under 35 U.S.C. 154(b) by 636 days.

(21) Appl. No.: 18/190,374

(22) Filed: Mar. 27, 2023

(65) Prior Publication Data

US 2023/0301790 A1 Sep. 28, 2023

Related U.S. Application Data

(60) Provisional application No. 63/324,148, filed on Mar. 27, 2022.

(51) Int. Cl.
*A61F 2/30* (2006.01)
*A61L 27/38* (2006.01)

(52) U.S. Cl.
CPC ........ *A61F 2/3094* (2013.01); *A61L 27/3808* (2013.01); *A61L 27/3826* (2013.01); *A61F 2002/30985* (2013.01)

(58) Field of Classification Search
CPC .......... A61F 2/3094; A61F 2002/30985; A61F 2/00; A61L 27/3808; A61L 27/3826; A61L 27/00; B29C 64/00; B29C 64/245; B33Y 30/00; B33Y 10/00; C12M 33/00; B22F 12/30; B22F 10/00; B22F 12/00
USPC .......................................................... 700/95
See application file for complete search history.

(56) References Cited

U.S. PATENT DOCUMENTS

| | | | | |
|---|---|---|---|---|
| 2011/0076665 | A1* | 3/2011 | Gatenholm | A01N 1/00 435/395 |
| 2014/0072777 | A1* | 3/2014 | Boday | C09D 11/30 524/517 |
| 2017/0165917 | A1* | 6/2017 | McKiel, Jr. | B29C 64/393 |
| 2018/0361667 | A1* | 12/2018 | Sternå | B33Y 50/02 |
| 2020/0406542 | A1* | 12/2020 | Bennett | B29C 64/245 |
| 2022/0105686 | A1* | 4/2022 | You | C12M 21/08 |
| 2022/0111579 | A1* | 4/2022 | Zhang | B29C 64/245 |
| 2022/0219402 | A1* | 7/2022 | Neill | B33Y 10/00 |
| 2022/0339859 | A1* | 10/2022 | Steele | B29C 64/223 |
| 2023/0399597 | A1* | 12/2023 | Schäfer | B33Y 50/02 |

* cited by examiner

*Primary Examiner* — Farah Taufiq
*Assistant Examiner* — Jonathan B Woo
(74) *Attorney, Agent, or Firm* — Own Innovation; James W. Hinton; Daniel Biggs

(57) ABSTRACT

A smart adjustable platform for a bioprinter is described. The adjustable platform comprises: a housing having an upper surface with a support region for providing support for 4D printing of a biomaterial; and at least one stimulator that is mounted within the housing, the at least one stimulator being configured to provide one or more stimuli to the biomaterial during printing and/or after printing for effecting a change in characteristic of the biomaterial including structure and/or morphology, wherein the at least one stimulator comprises a mechanical stimulator and/or an electromagnetic stimulator.

18 Claims, 18 Drawing Sheets

SMART PLATFORM BIOPRINTING BED WITH AT LEAST ONE CONTROLLABLE STIMULATOR

CROSS-REFERENCE

This application claims the benefit of U.S. Provisional Patent Application No. 63/324,148 filed Mar. 27, 2022; the entire contents of Patent Application 63/324,148 is hereby incorporated by reference.

FIELD

The present disclosure relates generally to an adjustable platform bed that may be used with a bio printer; and more particularly to an adjustable platform bed that has at least one controllable stimulator for applying at least one stimulus to a printed biomaterial.

BACKGROUND

Regenerative medicine and bioprinting combine medical aspects, cells, molecular biology, materials science, and bioengineering for various purposes such as to regenerate, repair, and/or replace tissues or organs. For example, 3D bioprinting may use cells and biomaterials rather than plastics and metals in an additive manufacturing process to create 3D biomaterials, like tissues, that are functional. These 3D biomaterials may be used in various areas such as drug R&D, regenerative medicine, and the creation of 3D cell cultures.

These 3D printed biomaterials are static; however, regenerative medicine and tissue engineering include seed cells, scaffolds, and the application of one or more stimulating factors. Accordingly, 4D bioprinting has been developed which involves the functional and/or structural transformation and maturation of printed cell-laden constructs over time. For example, tissue engineering scaffolds may be used to deliver specific cells to a damaged site and to act as a medium through which stimulation may be provided, with the help of an appropriate structure, similar in composition to natural tissue. Scaffolds mimic natural tissue's mechanical properties and biological properties, to provide in vivo support, optimum diffusion of nutrients, and encourage cellular communication, which is part of tissue engineering.

Recently, the application of physical stimulation in tissue engineering has shown great potential in disease treatment, clinical Contract Research Organization (CRO), and study of certain cellular mechanisms. For example, the application of an alternative magnetic field on cell viability and apoptotic death rate was studied and it was found that there may be a possible Alternating Magnetic Field (AMF) effect during clinical magnetic hyperthermia (Wang et al., 2013).

As another example, cell-seeded scaffolds may be implanted in a patient to produce new tissue in damaged organs or to replace missing organs. However, rapid and complete regeneration of tissue or organs is a challenging problem because transplanted cells may be easily lost in host tissues and have low survival rates. Furthermore, the potential for defective cells to migrate to the implant site may lead to undesirable complications.

In order to deal with the loss of cellular function at the donor site and uncontrollable differentiation to improve the success of stem cell transplantation in regenerative medicine, cellular behaviour may be manipulated. Examples of cellular behaviour that may be manipulated in vitro and in vivo, include cell proliferation, cell migration, cell differentiation, and other cellular processes. Cell behaviour may be manipulated by selecting a particular scaffold material, a surface topography for the scaffold, and applying one or more stimulating factors. For example, some studies have shown that biophysical stimulation may influence cell behaviors such as cell proliferation and cell differentiation which may help with tissue repair. However, applying inappropriate physical stimulating factors may cause cell death or have no effect. As a result, selecting and applying a suitable stimulating factor has the potential to produce cell-seeded scaffolds that may improve or augment their reparative effect on tissue. Furthermore, moving the printed biomaterials to other equipment for applying the stimulating factor may result in less realistic or less effective results. Accordingly, there is a need for a platform that can be used to test and alter printed biomaterials through functional stimulation during or after printing of the 3D biomaterials.

SUMMARY OF VARIOUS EMBODIMENTS

In one broad aspect, in accordance with the teachings herein, there is provided in at least one embodiment an adjustable platform for a bioprinter, wherein the adjustable platform comprises: a housing having an upper surface with a support region for providing support for 4D printing of a biomaterial; and at least one stimulator that is mounted within the housing, the at least one stimulator being configured to provide one or more stimuli to the biomaterial during printing and/or after printing for effecting a change in characteristic of the biomaterial including structure and/or morphology, wherein the at least one stimulator comprises a mechanical stimulator and/or an electromagnetic stimulator.

In at least one embodiment, the platform comprises a base plate at an upper surface thereof for providing the support region for 3D bioprinting of the biomaterial, the base plate being conductive to transmit the one or more stimuli to the biomaterial.

In an aspect, in accordance with the teachings herein, there is provided in at least one embodiment an adjustable platform for a bioprinter, wherein the adjustable platform comprises: a housing having an upper surface with a support region having a base plate at an upper surface thereof for receiving biomaterial, the base plate being conductive to transmit one or more stimuli to the biomaterial for 4D printing of the biomaterial; and at least one stimulator that is mounted within the housing and coupled to the base plate, the at least one stimulator being configured to provide one or more stimuli to the biomaterial during printing and/or after printing for effecting a change in characteristic of the biomaterial including structure and/or morphology, wherein the at least one stimulator comprises a mechanical stimulator and/or an electromagnetic stimulator.

In at least one embodiment, the mechanical stimulator comprises at least one piezoelectric transducer that is located underneath the base plate and is electrically coupled to a controller for receiving a control signal therefrom to generate one or more mechanical stimuli with a controllable amplitude, frequency, and/or duration, the one or more mechanical stimuli being transmitted to the biomaterial during and/or after printing of the biomaterial.

In at least one embodiment, the electromagnetic stimulator comprises at least one electromagnetic coil that is laterally offset from a center of the base plate and is electrically coupled to a controller for receiving a control signal therefrom to generate one or more electromagnetic stimuli with a controllable amplitude, frequency and/or duration, the one or more electromagnetic stimuli being transmitted to the biomaterial during and/or after printing of the biomaterial.

In at least one embodiment, the electromagnetic stimulator comprises two or more electromagnetics coils that are spaced apart from one another and at and opposite sides of the base plate to provide different electromagnetic stimuli to different regions of the support region of the platform.

In at least one embodiment, a first set of the electromagnetic coils are arranged to generate EM fields in the XY plane, and a second set of the electromagnetic coils are arranged to generate additional EM fields in the Z plane.

In at least one embodiment, the platform further comprises a thermal stimulator that comprises at least one thermoelectric cell that is located under the base plate and is electrically coupled to a controller for receiving a control signal therefrom to generate one or more thermal stimuli with a controllable amplitude and duration.

In at least one embodiment, the thermal stimulator comprises two thermoelectric cells that are spaced apart from one another to provide different thermal stimuli to different regions of the base plate.

In at least one embodiment, the thermal stimulator also comprises a heat sink and/or a fan that are thermally coupled to the support region of the platform for conducting heat away from the support region or conducting heat towards the support region during use depending on a temperature differential between a temperature at the support region and another temperature at the heat sink.

In at least one embodiment, the platform further comprises at least one electrical stimulator that comprises an electrode for providing an electrical stimulus to the biomaterial.

In another broad aspect, in accordance with the teachings herein, there is provided in at least one embodiment a bioprinter system for 4D printing of biomaterials, wherein the bioprinter system comprises: a housing; a frame mounted to the housing defining an incubator chamber; a frame; a printing head that is movably coupled to the frame for printing the biomaterials; and an adjustable platform that is moveably coupled to the frame, wherein the adjustable platform is defined according to any of the embodiments described herein.

In at least one embodiment, the frame comprises at least one guide rail and a lead screw and the adjustable platform is moveably coupled to the at least one guide rail via a slide bushing and the adjustable platform is moveably coupled to the lead screw via a worm gear sleeve.

In another broad aspect, in accordance with the teachings herein, there is provided in at least one embodiment a method for 4D printing of biomaterial structures, wherein the method comprises: 3D printing one or more biomaterial structures; and applying at least one stimulus to the one or more biomaterial structures during and/or after bioprinting using an adjustable platform that is defined according to any one of the embodiments described herein, wherein the at least one stimulus comprises one or more mechanical stimuli and/or one or more electromagnetic stimuli that are generated from within the adjustable platform.

In at least one embodiment, the method further comprises applying one or more electrical stimuli to the one or more biomaterial structures during and/or after printing.

In at least one embodiment, the method further comprises applying one or more thermal stimuli to the one or more biomaterial structures during and/or after printing.

In at least one embodiment, the one or more thermal stimuli are applied to provide a temperature-controlled heating or cooling step to facilitate cross-linking in bioink structures used to print the one or more biomaterial structures.

In at least one embodiment, the method comprises controlling the amplitude, frequency, and/or duration, of the one or more stimuli to affect shape, morphology and/or at least one characteristic of the one or more printed biomaterial structures.

In at least one embodiment, the method comprises applying the one or more mechanical stimuli, the one or more electromagnetic stimuli, the one or more thermal stimuli and the one or more electrical stimuli separately.

In at least one embodiment, the method comprises applying any combination of the one or more mechanical stimuli, the one or more electromagnetic stimuli, the one or more thermal stimuli and the one or more electrical stimuli simultaneously.

In at least one embodiment, the one or more electromagnetic stimuli include static or oscillating magnetic fields.

In at least one embodiment, the one or more electromagnetic stimuli are applied for developing bio-aligned arrays when magnetic nanoparticles are in bioink used to print the one or more biomaterial structures.

In at least one embodiment, the one or more mechanical stimuli are applied to provide surface treatment to the one or more printed biomaterial structures.

In at least one embodiment, the one or more stimuli optionally include thermal stimuli and the one or more stimuli is applied to perform crosslinking of polymer, hydrogel, or bioink chains used to print the one or more biomaterial structures.

In at least one embodiment, the biomaterial comprises bioprinted bioink.

It will be appreciated that the foregoing summary sets out representative aspects of embodiments to assist skilled readers in understanding the following detailed description. Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1A:
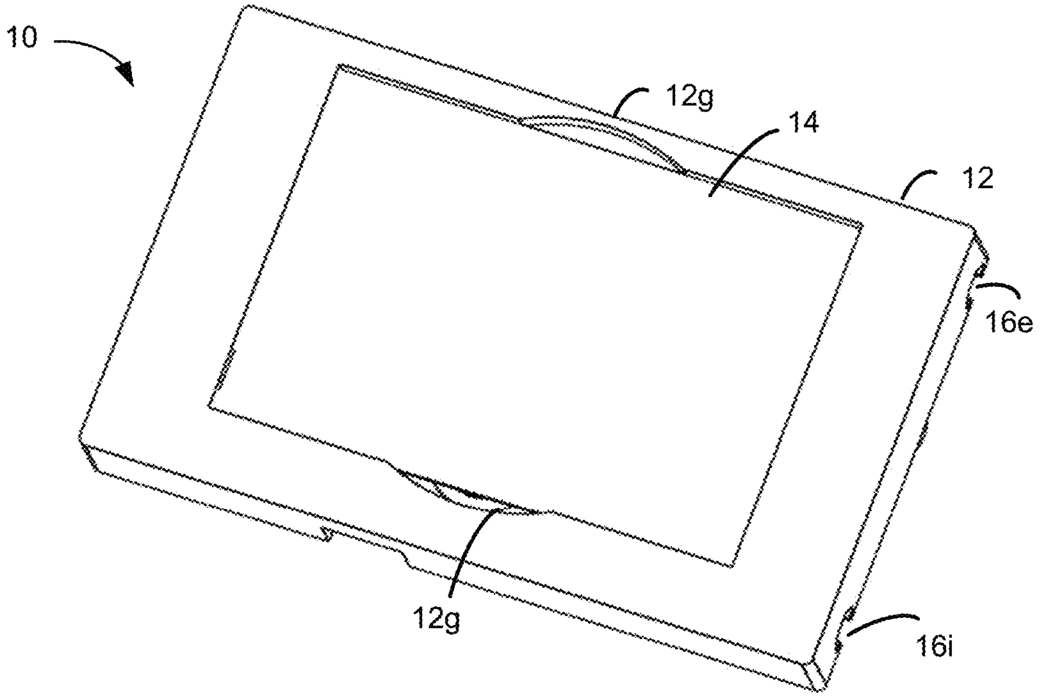
FIGS. 1A and 1B are front and rear perspective views of an example embodiment of an adjustable platform bed that can provide in situ stimulation for bioprinters in accordance with the teachings herein.

Further aspects and features of the example embodiments described herein will appear from the following description taken together with the accompanying drawings.

DETAILED DESCRIPTION OF THE EMBODIMENTS

The headings and Abstract of the Disclosure provided herein are for convenience only and do not interpret the scope or meaning of the embodiments.

Various embodiments in accordance with the teachings herein will be described below to provide examples of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the Figures to indicate corresponding or analogous elements or steps. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

It should also be noted that the terms "coupled", or "coupling" as used herein can have several different meanings depending on the context in which these terms are used. For example, the terms coupled, or coupling can have a mechanical or electrical connotation. For example, as used herein, the terms coupled or coupling can indicate that two elements or devices can be directly connected to one another or connected to one another through one or more intermediate elements or devices via an electrical or magnetic signal, electrical connection, an electrical element or a mechanical element depending on the particular context. Furthermore, certain coupled electrical elements may send and/or receive data.

Unless the context requires otherwise, throughout the specification and claims which follow, the word "comprise" and variations thereof, such as, "comprises" and "comprising" are to be construed in an open, inclusive sense, that is, as "including, but not limited to".

Various terms used throughout the present description may be read and understood as follows, unless the context indicates otherwise: singular articles and pronouns as used throughout include their plural forms, and vice versa; similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

Reference throughout this specification to "one embodiment", "an embodiment", "at least one embodiment" or "some embodiments" means that one or more particular features, structures, or characteristics may be combined in any suitable manner in one or more embodiments, unless otherwise specified to be not combinable or to be alternative options.

As used in this specification and the appended claims, the singular forms “a”, “an”, and “the” include plural referents unless the content clearly dictates otherwise. It should also be noted that the term “or” is generally employed in its broadest sense, that is, as meaning “and/or” unless the content clearly dictates otherwise.

Similarly, throughout this specification and the appended claims the term “communicative” as in “communicative pathway”, “communicative coupling”, and in variants such as “communicatively coupled”, is generally used to refer to any engineered arrangement for transferring and/or exchanging information. Examples of communicative pathways include, but are not limited to, electrically conductive pathways (e.g., electrically conductive wires, physiological signal conduction), electromagnetically radiative pathways (e.g., radio waves), or any combination thereof. Examples of communicative couplings include, but are not limited to, electrical couplings, magnetic couplings, radio couplings, or any combination thereof.

Throughout this specification and the appended claims, infinitive verb forms are often used. Examples include, without limitation: “to detect”, “to provide”, “to transmit”, “to communicate”, “to process”, “to route”, and the like. Unless the specific context requires otherwise, such infinitive verb forms are used in an open, inclusive sense, that is as “to, at least, detect”, “to, at least, provide”, “to, at least, transmit”, and so on.

A portion of the example embodiments of the systems, devices, or methods described in accordance with the teachings herein may be implemented as a combination of hardware or software. For example, a portion of the embodiments described herein may be implemented, at least in part, by using one or more computer programs, executing on one or more programmable devices comprising at least one processing element, and at least one data storage element (including volatile and non-volatile memory). These devices may also have at least one input device (e.g., any combination of a keyboard, a mouse, a touchscreen, and the like) and at least one output device (e.g., any combination of a display screen, a printer, a wireless radio, and the like) depending on the nature of the device.

It should also be noted that there may be some elements that are used to implement at least part of the embodiments described herein that may be implemented via software that is written in a high-level procedural language such as object-oriented programming. The program code may be written in C, C++ or any other suitable programming language and may comprise modules or classes, as is known to those skilled in object-oriented programming. Alternatively, or in addition thereto, some of these elements implemented via software may be written in assembly language, machine language, or firmware as needed. In either case, the software comprises machine executable code.

At least some of the software programs used to implement at least one of the embodiments described herein may be stored on a storage media or a device that is readable by a general or special purpose programmable device. The software program code comprises machine executable code that, when read and executed by the programmable device, configures the programmable device to operate in a new, specific, and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The program code may be preinstalled and embedded during manufacture and/or may be later installed as an update for an already deployed computing system. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

Accordingly, any module, unit, component, server, computer, terminal or device described herein that executes software instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information, and which can be accessed by an application, module, or both. Any such computer storage media may be part of the device or accessible or connectable thereto.

Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, software application or software module herein described may be implemented using computer readable/executable instructions that may be stored or otherwise held by such computer readable media and executed by the one or more processors.

The teachings herein relate to stimulation techniques that can be applied to printed biomaterials (e.g., engineered biomaterials) to cause various changes in bio-printed structures that may be created using bioink and 3D printing technology. This may be done using an adjustable platform bed system to gradually (e.g., continuously) cause morphological and/or functional changes in complex bio-printed specimens such as, but not limited to, scaffolds, implants, prostheses, tissues, organs, cancer cells, epithelial cells, fibroblasts, immune cells, endothelial cells, and/or nerve cells for example. For example, in situ stimulation can be used to facilitate hydrogel or bioink cross-linking in the printed biomaterials. In another example, in situ stimulation can be applied to bio-printed organoids or spheroids, such as tumor cells, to form one or more toroids having one or more diameters.

The inventor has found that it is possible to optimize the application of or more stimulators to provide in situ hybrid actuation during and/or after the printing of 3D biomaterials to achieve a final state of 4D printed constructs with added functional and/or structural properties. It should be noted that the terms specimens or samples means biomaterials that are produced using 4D printing techniques described herein.

The teachings herein may be used in various applications such as, but not limited to, biomedical implants and devices, tissue engineering, cancer research, drug discovery, regenerative medicine, and health care products. For example, the teachings herein may be used to adjust the production of biomaterial by controlling stimulation that is applied to the biomaterial in situ to change the shape and/or functionality of the printed biomaterials. This may involve changes to surface topography, substrate stiffness, compression, and stretching properties. Further examples include applying stimulation to 3D cell cultures to change one or more of their characteristics such as cell proliferation, cell migration, and/or gene delivery or modify the cell cultures for use in various applications including bio-actuation, bio-robotics, and/or bio-sensing.

In accordance with the teachings herein, stimulation may be performed using a bioprinting platform which may be referred to as an adjustable platform bed system, a smart bed or a smart bioprinting platform, that has at least one stimulator that can be used to apply one or more stimuli to biomaterial that is being created in a bioprinter to effect structural and/or functional changes to the printed biomaterials thereby modifying one or more properties of the printed biomaterials during printing and/or after printing.

The applied stimulation may be static or dynamic to have various affects, such as affecting the growth of a three-dimensional scaffold. For example, the bio-printed specimens may be an extracellular matrix or bio-printed scaffolds that may receive stimulation from several stimulators in parallel (e.g., at the same time) or in series (e.g., sequentially in time). The stimuli may affect the stability, swelling potential, and rheology of a polymerized bio-printed scaffold, depending on the stimuli that is being applied. As an example, stimulation may be applied to cancerous physical cell cultures in predetermined time intervals. In this case, one or more stimulators may be configured to be used with bioprinting to quantify and change characteristics of a bio-printed physical cell culture over time. In another example, physical stimuli may be applied at predetermined intervals, which increases the storage stability of composite bioink formulations and affects extrusion characteristics. In another example, in some cases electromagnetic stimuli may be used enzymatically dissociate printed biomaterials to isolate non-invasive cancer cells and invasive cancer cells.

Examples of stimuli include thermal stimuli, ultrasound stimuli, photo-stimulation, as well as electrical and/or electromagnetic stimuli. The application of stimuli has certain advantages such as cost-effectiveness, long life, ease of processing, and high reproducibility, which each facilitate large-scale operation. For example, certain stimuli, such as Electrical Stimuli (ES), Mechanical Stimuli (MS), Electro-Magnetic (EM) and/or Thermal Stimuli (TS) can be used to effectively relieve pain, improve blood circulation, reduce vascular and skeletal muscle tension, reduce edema and improve joint movement. These stimuli can be applied at different rates using the adjustable platform described herein.

For example, studies have shown that electrical stimuli may effectively manipulate cell behavior in vitro and in vivo. In one study, Jatinen et al. demonstrated that the mouse myoblast cell line undergoes dramatic changes in cell morphology, viability, structure, and adhesion under pulsed monophasic currents. By controlling the parameters used for ES, the neurotic outgrowth of Neural Precursor Cells (NSCs) may be improved, and the differentiation of NSCs may also be manipulated. In the human body, every cell is subjected to some form of stimulation, and local bioelectrical signals affect cells in a variety of tissues. For example, ES triggers cells to deliver signals through intrinsic pathways, resulting in direct cell activity, including migration, differentiation, proliferation, etc. In addition, the inventor has found that ES may be used synergistically with other techniques to reduce the overall cost of the bioprinting process. ES therefore has the potential to alleviate some of the current problems in tissue engineering and reconstructive medicine.

The benefits of using mechanical stimuli include the positional accuracy with which mechanical stimuli can be applied. For instance, ultrasound can provide spatial and temporal control with millimeter accuracy since a focused ultrasound beam may be used to trigger drug release via localized heating induced by the deposition of acoustic energy at a focused area.

Recently, magnetically responsive hydrogel, which is one kind of smart hydrogel, has been introduced into biomedical applications for improving the biological activities of cells, tissues, or organs. This is mainly due to the magnetic response of this hydrogel to the external magnetic field and the acquisition of functional structures to remotely regulate the physical, biochemical and mechanical properties of the environment around cells, tissues, or organs. Recent studies have shown that magnetic hydrogels can also be used in a drug delivery and targeting system.

Stimulation of biomaterials may also be performed using surface treatment that can result in a change in the shape and/or morphology of the surface of the biomaterials that may provide better biocompatibility. For example, in situ and post-annealing coating are two common approaches to synthesize polymer coated IONPs in which polymers are coated onto the surface of IONPs during the synthesis process (Fajaroh et al., 2012). In another example, surface treatment may be performed using external atmospheric plasma, external low power laser, external photo cure stimulation, and/or smart bed physical stimulation (as described herein using electromagnetic fields, thermal energy and/or vibrational energy). The word external as used herein means external to the smart bed platform. An implementation that may be used to provide external atmospheric plasma, external low power laser, and external photo cure stimulation is described in PCT published patent application WO2019180749, entitled "Automatic Additive Multi Stage Portable Three Dimensional Device for Manufacturing of Hard and Soft Organs" and published on Sep. 26, 2019, which is hereby incorporated in its entirety herein. By using these stimulations, the physio-chemical properties of the surface of a polymer may be changed in a way that makes it attractive for a variety of biological compounds, or, on the contrary, makes the polymer exhibit antibacterial or cytotoxic properties, thus making the polymer useful in orthopedic and dental implants and prostheses.

Both peptide orientation and surface concentration may be achieved by varying the solution pH or by applying stimulation during bioprinting. The surface functionalization of an implantable device with bioactive molecules can overcome adverse biological responses by promoting specific local tissue integration. Accordingly, printed biomaterials with surface treatment may be used in the treatment of osteoporosis and/or result in better osteointegration when used in bone implants. The adjustable stimulator platforms described herein may also be used for the development of orthopedic implants by performing tests on 3D cell cultures that are developed for artificial bones and other orthopedic implants for various parts of the body such as in the elbow, the wrist, the ankle, etc.

Referring now to FIGS. 1A-1G, shown therein is an example embodiment of an adjustable platform 10 in accordance with the teachings herein which can provide stimulation during and/or after the printing of a biomaterial in a bioprinter. The adjustable platform 10 may be used in a sealed 3D bioprinting system (e.g., bioprinter). The adjustable platform 10 includes a substrate that defines a smart bed (e.g., plate 14) which contains one or more stimulators for applying one or more stimuli to one or more printed parts or scaffolds that are disposed on the smart bed to change the shape and/or characteristics of the one or more printed biomaterial parts or scaffolds. The printed biomaterial may be made using fused deposition modelling (FDM) or an injection print head.

The adjustable platform 10 includes a housing or frame 12 with various compartments or recesses for receiving certain components that can be used for applying different types of stimuli. The housing 12 is a rigid structure that maintains all of the electronic and mechanical parts of the adjustable platform 10 in place. The housing 12 may be made using Acrylonitrile Butadiene Styrene (ABS) plastic or another suitable material. In this example embodiment, the adjustable platform includes stimulator elements that can provide any combination of thermal stimuli, mechanical stimuli and electromagnetic stimuli including providing each type of stimuli separately or two different types of stimuli or all of these stimuli at the same time. For instance, in the example embodiment shown in FIGS. 1A-1G, the adjustable platform 10 comprises two controllable electromagnetic coils for electromagnetic stimulation, one piezoelectric actuator (which may also be called a piezoelectric transducer) for mechanical stimulation, and an adjustable thermal stimulator that lie beneath a bed region or printing bed area of the platform 10 that is defined by a plate that can support any cell culture plate, petri dishes or other plates upon which the bioprinting is performed. An alternative embodiment of an adjustable platform 600 also includes an electrical stimulator and additional electromagnetic stimulators for additionally providing one or more electric stimuli and different types of electromagnetic fields as will be described with reference to FIGS. 6A-6E.

However, in alternative embodiments, an adjustable platform may include just one type of stimulator to provide one of thermal, mechanical, electrical and electromagnetic stimuli or two different types of stimulators to provide two different types of stimuli such as thermal stimuli and electromagnetic stimuli; thermal stimuli and mechanical stimuli; mechanical stimuli and electromagnetic stimuli; thermal stimuli and electric stimuli; electromagnetic stimuli and electric stimuli; or mechanical stimuli and electrical stimuli; for example. In another embodiment any three or all four of thermal stimuli, electric stimuli, electromagnetic stimuli and mechanical stimuli may be provided. In at least one embodiment, the various stimulators may be operated to affect the bioprinting process using a closed-loop control path.

The adjustable platform 10 includes a removable plate 14, which may be referred to as a base plate, at an upper surface of the frame 12 upon which a container, such as a petri dish, can be placed and the biomaterial can be produced. Accordingly, the plate 14 provides a support region above which biomaterial may be printed. The frame 12 may optionally include a rectangular cutout that is sized to receive the plate 14 and one or two gaps 12*g* along one or two sides of the rectangular cutout to allow a user to access an edge and portion of the lower surface of the plate 14 to remove it from the frame 12. The gaps 12*g* also allow for a petri dish or culture dish to be placed on the plate 14. The plate 14 generally overlays and is coupled to one or more stimulators. The plate 14 may be made from steel.

In at least one alternative embodiment, there may be two or more plates that are generally located where the removable plate 14 is located which may be spaced apart from one another thereby defining two or more beds which may each be associated with different stimulators such as different electromagnetic coils and/or different thermoelectric cells.

Figure 1B:
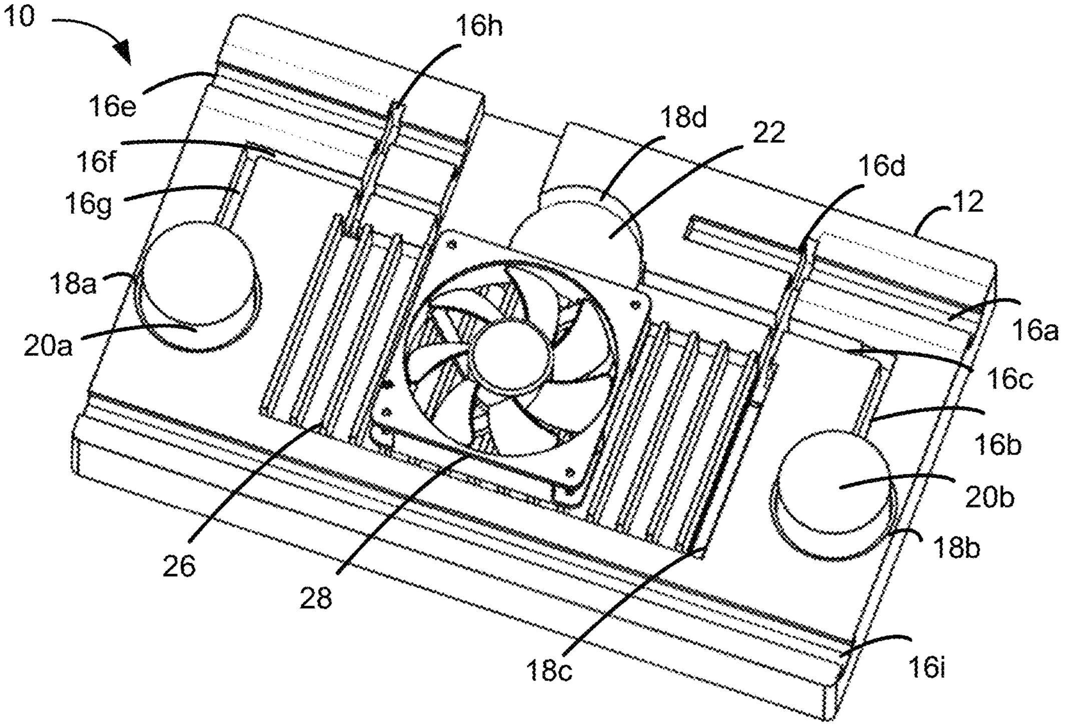
Figure 1C:
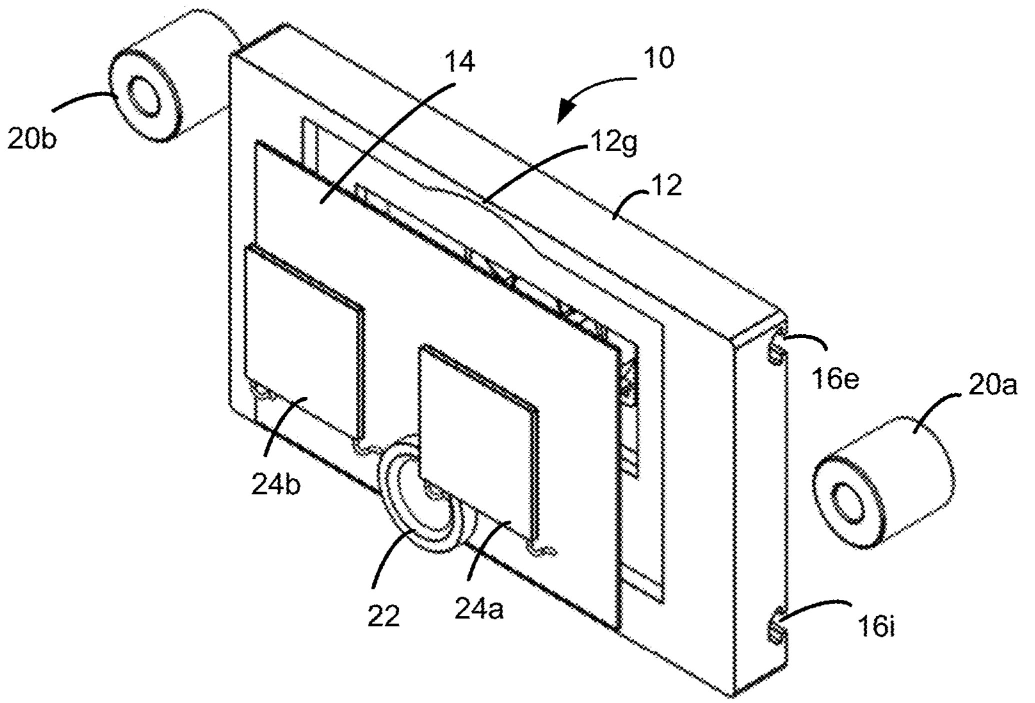
FIGS. 1C, 1D and 1E are front perspective, top and rear perspective exploded views of the example embodiment of the adjustable platform bed.
Figure 1D:
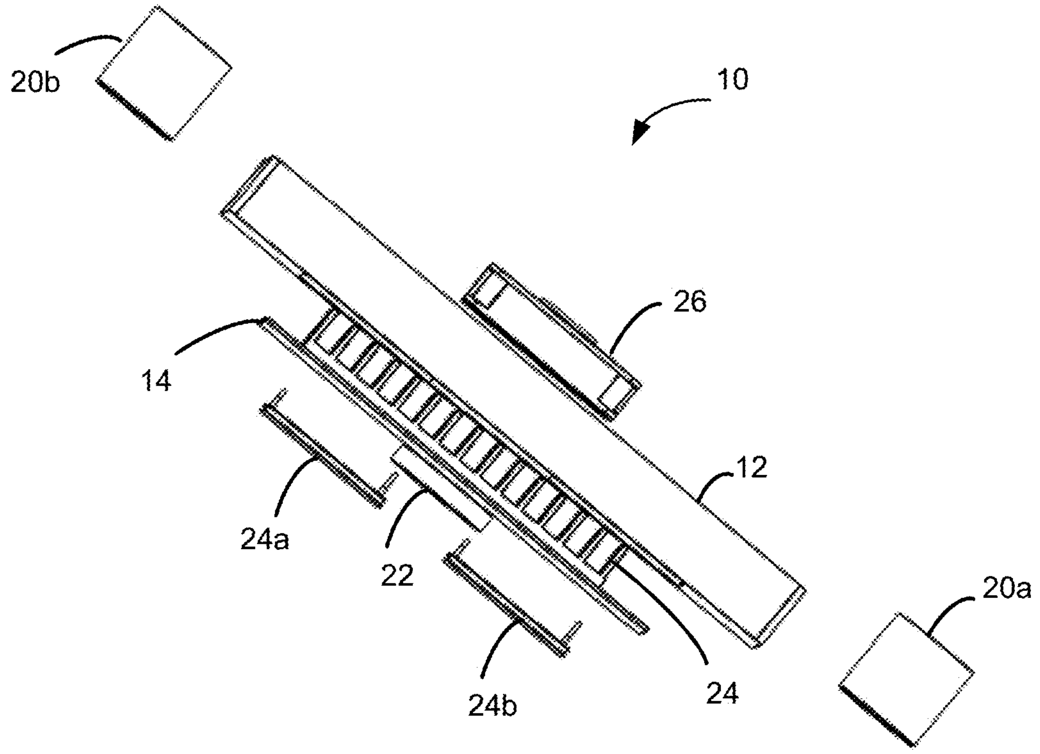
Figure 1E:
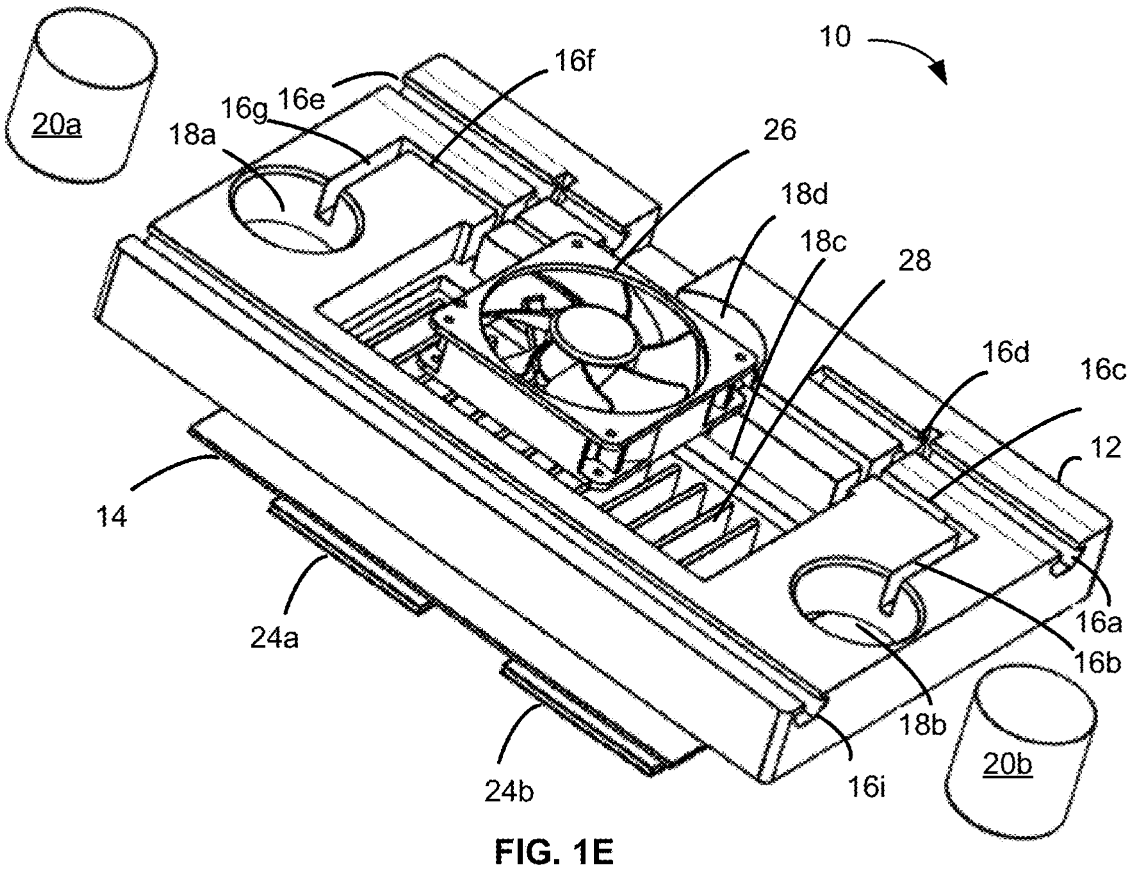
Figure 1F:
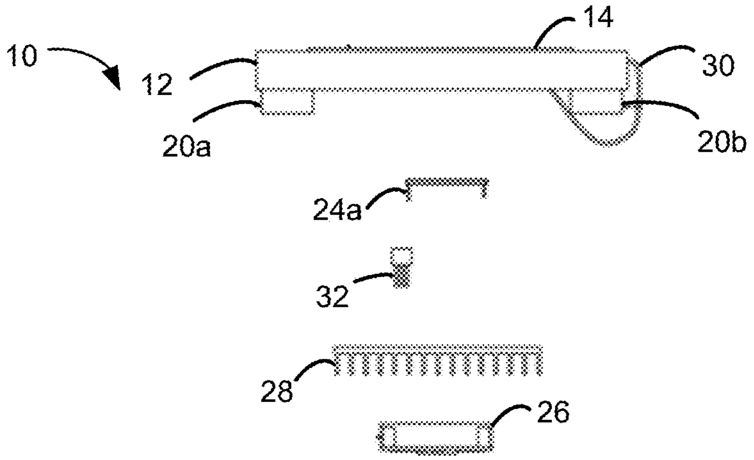
FIG. 1F is a side partially exploded view of the example embodiment of the adjustable platform bed which also shows a thermal sensor.
Figure 1G:
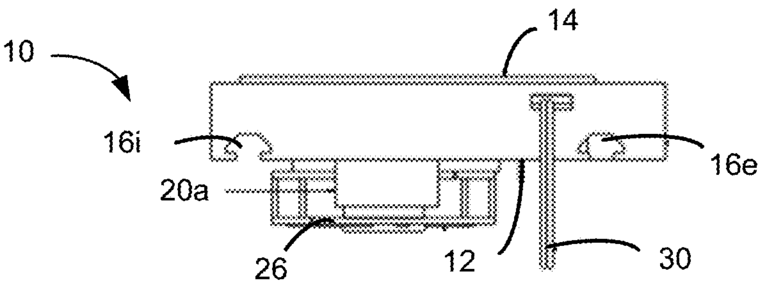
FIG. 1G is a side view of the example embodiment of the adjustable platform bed which also shows the thermal sensor.

The adjustable platform 10 includes various grooves or channels on an underside of the frame 12 so that various wires may be run to the different electrical components of the adjustable platform 10 that are used to provide different types of stimuli. For example, the adjustable platform 10 may include channels 16*a*-16*h*. One example of a layout for channels 16*a*-16*h* is shown in FIG. 1B, for example. However, other layouts may be used for channels 16*a*-16*h*.

The adjustable platform 10 includes indents or receptacles 18*a* to 18*d* for receiving various physical components that are coupled to the housing 12. For example, receptacles 18*a* and 18*b* may be used to receive two electromagnetic coils 20*a* and 20*b*. The receptacle 18*d* may be used to receive a mechanical actuator 22, which may be implemented using at least one piezoelectric transducer. The adjustable platform 10 also includes thermoelectric cells 24*a* and 24*b*. The plate 14 is coupled to these various elements through thermal, electromagnetic or mechanical coupling and is made of material that allows for the transmission of thermal, electromagnetic or mechanical energy therethrough so that the biomaterial that is above the plate 14 may receive various any combination of thermal, electromagnetic and/or mechanical energy stimuli during use including just a single type of energy.

In at least one embodiment, the piezoelectric transducer 22 and each of the electromagnetic coils may have a center to center distance of between about 1 cm and about 25 cm.

In at least one embodiment, the thermoelectric cells 24*a*, 24*b* may have a center to center distance from the piezoelectric transducer of between about 1 cm to about 5 cm.

In at least one embodiment, the thermoelectric cells may be operated separately or together at the same time.

The adjustable platform 10 uses the piezoelectric transducer 22 to generate mechanical stimuli. The intensity and frequency of the mechanical energy generated by the piezoelectric transducer 22 may be controlled via various means such as by using closed-loop control with a PID controller, for example. The piezoelectric transducer 22 may be used to generate high-frequency sound waves that provide mechanical energy to the plate 14 so that the plate 14 vibrates. The vibration of the plate 14 results in a force being applied to the surface of one or more printed biomaterials that are above the plate 14, which may result in a change in the surface of one of more of the printed biomaterials. The mechanical stimuli may also be modulated to control physical, chemical, and/or biological factors (e.g., interstitial effect, media impact velocity) that affect cell growth. In at least one embodiment, continuous mechanical stimulation may be provided for a predetermined time period (e.g., about 30 minutes) so that the bioprinted specimens are subject to indirect interstitial pressure through vibration that is controlled with intensity and frequency. The piezoelectric transducer 22 may be applied to provide a pressure of between about 0 Pa to about 20 Pa with a frequency in the kHz range and may be applied to provide resonance. The high-intensity vibration can induce apoptosis or cell death, while low-intensity vibration can promote cell survival and metabolic activity. Also, high-frequency vibration can enhance cell proliferation and differentiation, while low-frequency vibration can promote bone formation and remodeling. For example, for deep tissue hyperthermia, frequencies may be in the range of about 50 MHz to about 1,000 MHz, while in superficial hyperthermia, higher frequencies in the range of about 900 MHz to about 2.45 GHz may be used. The mechanical stimuli that are used (e.g., the intensity, frequency, and duration) depend on the desired cellular response to achieve the desired effects.

The electromagnetic coils 20*a* and 20*b* are used by the adjustable platform 10 to generate electromagnetic stimuli which may be static or dynamic magnetic fields. The frequency of the electromagnetic fields may be between about 0 Hz to about 100 MHz. The electromagnetic fields may be applied for predetermined time periods between about 1 second to about 60 days. The electromagnetic field may be applied continuously or may be applied periodically. The electromagnetic coils 20*a*, 20*b* may be operated separately to provide one EM field or at the same time to provide two EM fields. The EM stimuli can affect cellular behavior through various mechanisms, including changes in ion channels, intracellular signaling pathways, and gene expression and have enhance cell proliferation, differentiation, and extracellular matrix synthesis. For example, low-frequency EM fields used for cell proliferation typically fall within the extremely low-frequency (ELF) range, which is typically between about 0 and about 300 Hz, and more preferably in the frequency range of about 7 Hz to about 50 Hz. For example, one study found that a 50 Hz magnetic field increased the proliferation of human bone marrow cells in culture, while another study found that a 16 Hz magnetic field increased the proliferation of human osteoblast cells.

The adjustable platform 10 also includes a receptacle 18*c* that receives a heat sink 26, and a fan 28, which together with the thermoelectric cells 24*a* and 24*b*, form the thermal stimulator which may be used for generating hot and cold thermal stimuli. The thermoelectric cells may have a size of about 0.8 $cm^2$ to about 5.9 $cm^2$ with 3 to 5 $cm^2$ being more common squared depending on the size of the adjustable platform 10. For example, the thermoelectric cells may have a size of about 4 $cm^2$. The heat sink 26 and fan 28 may be similar to those used with computer motherboards. The heat sink 26 is mounted within the housing 12 and is in thermal contact with the thermoelectric cells 24*a* and 24*b*. The fan 28 is mounted adjacent to the heat sink 26 and is in thermal contact with the heat sink 26. The fan 28 may be an adjustable speed fan.

Thermal energy flows from a high-temperature location either from the thermal stimulator to the printed biomaterial or from the printed biomaterial to the thermal stimulator depending on whether hot or cold thermal stimuli are being generated. When heat energy is discharged from a low-temperature area through the thermoelectric cells 24*a*. 24*b*, some of the heat energy that flows into the thermal stimulator is not released as heat and is instead converted into electrical energy in the device, emitting DC voltage and current. A higher voltage can be obtained by including more thermoelectric cells in the thermal stimulator.

The adjustable platform 10 can apply a hot thermal stimulus by using one of the thermoelectric cells 24*a*, 24*b* that is configured to generate heat which is then thermally conducted to the printed biomaterial for a first time period after which the thermoelectric cell 24*a*, 24*b* is controlled to stop generating heat and the fan 26 can be operated which, along with the heat sink 24, will dissipate heat and cool down the printed biomaterial for a second time period.

Alternatively, the adjustable platform 10 can apply a cold thermal stimulus by using one of the thermoelectric cells 24*a*, 24*b* that is configured to generate a lower temperature (e.g., freezing) which removes heat that is thermally conducted from the printed biomaterial for a first time period after which the thermoelectric cell 24*a*, 24*b* is controlled to stop generating a lower temperature (e.g., stop freezing) and if the temperature of the thermoelectric cells 24*a*, 24*b* and the printed biomaterial is lower than the surroundings of the adjustable platform 10, then the heat sink 24 will allow for heat to be transmitted to the printed biomaterial to warm it up for a second time period.

The bioprinter platform 10 may also include a thermal sensor 30 that is connected to the thermoelectric cells 24*a* and 24*b*, which can be used in thermal regulation of the thermal stimuli that are provided by the thermoelectric cells 24*a* and 24*b* to the printed biomaterial. An example of this is further discussed with respect to FIG. 2B.

The bioprinter adjustable platform 10 may also include an electrical connector 32 which is used to electrically couple the stimulators/actuators, e.g., the electromagnetic coils 20*a*, 20*b*, the piezoelectric transducer 22, the thermoelectric cells 24*a*, 24*b* and the fan 28, to a controller board that is part of the bioprinter so that the stimulators/actuators can receive control signals that control the generation of the various stimuli and certain properties of the stimuli such as amplitude and/or frequency, for example. In an alternative embodiment, instead of using electrical connector 32, wireless communication may be used when the adjustable platform 10 and the controller include a transmitter/receiver (e.g., Bluetooth radios may be used to facilitate Bluetooth communication).

In general, the adjustable platform 10 may be used to provide stimuli in various ways to the printed biomaterial. For example, a first stimulus such as a mechanical stimulus, may be applied to one or more printed parts on the bioprinter platform. The printed parts may collectively define a set of biomaterials that are printed in layers and may include scaffolds, for example. A stimulus may be applied through the first printed layer and may then travel through the first printed layer so that it may be applied to each of the other printed layers individually. The various stimulators may be used to affect the printed material differently.

Stimulation may be applied via the adjustable platform 10 for a predefined period of time at a desired intensity such as providing a certain type of stimulus for at least about 1 second. This may be done for various reasons such as exposing a first printed layer to direct interstitial stimulation from the adjustable platform 10 and then conducting the stimulation indirectly through the transfer of physical energy to other bioprinted layers.

In at least one embodiment, the stimulus may be controlled and delivered such that the stimulus is received at each layer of the printed material at a set of predetermined time intervals. The time and intensity parameters may be provided manually by a user of the bioprinter via a user interface of the bioprinter or via a mobile application, or these stimulation parameters may be obtained from memory and automatically defined so that certain stimulus types are received at different layers of the printed biomaterial at different times. One or more stimulations for the printed biomaterial may be defined in stored data for generating dynamic or static stimuli where a static stimulus is a constant stimulus (e.g., a constant amplitude with no variation) and a dynamic stimulus means a stimulus with an oscillating parameter such as amplitude.

A stimulus type refers to the physical nature of the stimulus. Accordingly, the different stimulus types may include, but are not limited to, electromagnetic, mechanical, thermal, electric stimuli or optical stimuli, for example, depending on the type of stimulators which are used.

The combination of various stimulators, e.g., the piezoelectric transducer and the electromagnetic coils or thermoelectric cells may have a center-to-center distance of between about 1 mm to about 250 mm. A set of base plates may be attached to an interface between a series of stimulators and the bioprinted parts or scaffold(s). In at least one of these embodiments, the series of the stimulators are coupled to the first layer of printed biospecimens with a steel bracket on at least one of the base plates.

In at least one embodiment, the bioprinted bioparts or scaffolds are in an enclosed chamber of a bioprinter, where the bioprinter also provides an external stimulator environment in terms of providing a stimulus that is not provided by the adjust platform 10. The enclosed chamber may be referred to as an incubation chamber. For example, in at least one embodiment, inside the bioprinter there may be modular head that may be used to provide an external stimulus to the bioprinted part that is on the adjustable platform 10 (e.g., the smart bed). For example, directly above the adjustable platform 10, there may be one or more actuators housed within the bioprinter chamber that can generate a low power laser or an atmospheric plasma to perform surface treatment on the bioprinted material and/or increase cell proliferation in cell based scaffolds. These actuators may be implemented in various ways some of which are discussed in PCT patent publication no. WO 2019180749.

Alternatively, in at least one embodiment, there are at least two plates on the bioprinter adjustable platform and at least one stimulator is coupled to one plate and at least one other stimulator is coupled to a different plate for cases in which a two plate fender is used to provide two plates for the bed.

In at least one embodiment, the thermal energy may be provided for a predetermined time period. In some cases, the electromagnetic energy may first be provided by the electromagnetic stimulator, and the thermal energy provided by the thermal stimulator is provided after the electromagnetic energy is provided. The effects of the electromagnetic and thermal energy on the printed biomaterial may interact and affect certain properties of the printed biomaterial such as its shape and certain surface characteristics such as surface structure, surface texture and/or surface tension.

In at least one embodiment, the electromagnetic and thermal stimulators may be controlled to provide electromagnetic and thermal energy in a predetermined direction and at a certain rate.

In at least one embodiment, the thermal stimulator may be operated simultaneously with the mechanical stimulator or the electromagnetic stimulator.

In at least one embodiment, provision of thermal stimulation may be prohibited when mechanical stimulation is first applied to a base plate that contains scaffolds or bioprinted for a 4D cell culture. In such embodiments, electromagnetic energy may also be provided to the cell culture and at least one of mechanical energy and electromagnetic energy may have an effect on growth of the 4D cell culture.

In at least one embodiment, the electromagnetic and thermal energy provided by the electromagnetic and thermal stimulators is in the same direction upwards to the bioprinted materials without cells. For example, bioprinting can also be performed without cells, using only biomaterials or bioinks to create scaffolds or structures that can be seeded with cells later. This approach can be useful for creating complex structures or for optimizing the physical and mechanical properties of the scaffold before cell seeding.

In at least one embodiment, there may be additional stimulators such as fourth, fifth, sixth, and seventh stimulators, and so forth. In such embodiments, larger base plates may be used, or more base plates may be used, and the stimulators may be positioned and configured to apply stimulation to a single physical cell culture, or at least one stimulator may apply stimulation to a first 3D cell culture and at least one other stimulator may apply stimulation to a different 3D cell culture on a common base plate or on different base plates.

Accordingly, in at least one embodiment, each stimulator may be coupled to the same plate (smart bed structure). In other embodiments, at least one stimulator may be connected to a second base plate that supports another petri dish or cell culture plate.

In at least one embodiment, a 3D cell culture sample may be bioprinted to have a volume that is at least about 20 μL. The 3D cell culture sample may include: (a) one or more cancer cells, (b) one or more viruses, (c) one or more human cells including but not limited to cancer cells, epithelial cells, fibroblasts, immune cells, endothelial cells, stem cells, nerve cells or (d) any combination of (a) to (c). In such cases, each stimulator of the adjustable bioprinting platform may be between 0.2 cm to about 20.0 cm in diameter and the thermal stimulators may be configured to generate heat so that the 3D cell culture is at a temperature between about −20 degrees Celsius to about 70 degrees Celsius. The thermal stimuli may be used as cross-linker for some bioinks such as, but not limited to, low temperature agarose, for example.

In general, the scaffolds that are used in bioprinting may have an extracellular matrix. The extracellular matrix may be composed of any combination of collagen, hydrogel, agarose, polyethylene glycol, alginate, hyaluronan acid, laminin, chitosan, composite, PCL, PLA, fibronectin, proteoglycans, and elastin. In at least one application, the bioink may include a concentration of its components of between about 1 mg/ml and 1000 mg/l. In at least one application, the bioink may include chemical cross-linkers with coaxial crosslinking.

In at least one embodiment, the bioprinter adjustable platform described herein may be used to apply a combination of different stimuli including mechanical and electromagnetic stimuli to a 3D bioink material containing a physical cell culture having an extracellular matrix. The extracellular matrix may behave as if collectively there is a set of mechanical actuators that are configured to three-dimensionally culture the physical cell culture while at the same time receiving electromagnetic energy from the electromagnetic stimulator. The combination of mechanical and electromagnetic stimuli may vary depending on the specific cell type and tissue for the bioprinted material. Mechanical stimulation can be applied to 3D bioink material containing a physical cell culture and extracellular matrix using a variety of techniques, such as compression, tension, or shear. In some cases, a bioreactor may be used to apply mechanical stimulation to the 3D bioink material in a controlled and reproducible manner. When there are multiple layers of bioprinted parts, each of these layers may be affected through using conductive layers (e.g., connective elements).

In at least one embodiment, mechanical stimulation may be applied by the mechanical stimulator to the printed biospecimens which receive indirect interstitial pressure through the mechanical vibration such as when a piezoelectric actuator is used as the mechanical stimulator. This may result in a portion of the physic al cell culture being separated from the extracellular matrix.

In at least one embodiment, the mechanical stimulator may be used to study cell mechanics and its alterations in cell and tissue homeostasis and pathology. Such studies may aid in understanding the mechanisms mediating cellular mechanical transduction, and matrix-elasticity modifications. Mechanical stimuli may also be used for modifying substrate nano-topography patterns, by applying nano-displacement through local nano-forces (internal or external to the cell, and vibration) which may have benefits for cell migration, proliferation, and/or morphology. For example, modifying nano-topography patterns for bioprinted specimens through mechanical stimuli may involve applying controlled forces at the nanoscale with specific amplitude, frequency, waveform, and duration to induce local deformation of the substrate. Accordingly, mechanical stimuli may also be used to study cell migration, cell proliferation and/or morphology of a 3D cell culture.

In at least one embodiment, the electromagnetic stimulator can be used to study to see the effect of variable frequency and/or intensity on printed biomaterials. For example, electromagnetic stimuli may be applied to affect intracellular signaling pathways and influence the intracellular microenvironment, which may be used for disease treatment, and/or wound healing. In another application, the electromagnetic stimulation may be used for testing of biocompatible conductive materials and biofilm. Electromagnetic stimuli may have applications to study various cellular activity including, but not limited to, cell migration, cell proliferation, cell differentiation, cell alignment, cell activity for specific therapeutic cancer drugs for migratory function, and cellular based non-invasive treatment of prosthetic joint infections. Electromagnetic stimuli may also change the shape and/or mechanical properties within printed biomaterial when bioink is used that has nano ferrite particles. In another example, electromagnetic stimulators may also be used in cell hyperthermia applications and their effects on the bio-printed scaffolds containing cells or tumors which may allow for killing tumor cells without damage to normal cells over time.

In at least one embodiment, the thermal stimulator may be used for cooling and warming bioprinted specimens. For example, the thermal stimulator may be used to apply thermal stimuli at certain times with certain intensities to control the thermal cycle and cell viability of the printed biomaterial. Thermal stimuli also have effects on bioink (e.g., bio-polymer thermal cross-linking), and may be used for thermal cycling (e.g., changing temperature by decreasing or increasing cold and heat stimulation) and may increase cell viability in cell laden printed scaffolds.

In at least one embodiment, all of the stimulators may be operated with a constant amplitude or an amplitude that varies according to a sinusoidal sequence thereby providing different intensities over time.

In at least one embodiment, the intensity of the different stimuli can be controlled for having several effects on the bioink for changing its shape with time.

In at least one embodiment, a method of using the bioprinter adjustable platform may include forming a bio-printed specimen using different stimuli. For example, over a time period, a substrate and an extracellular matrix may be formed. The substrate and the extracellular matrix may then be subjected to different types of stimuli from different types of stimulators over time to create a three-dimensional cell culture. A substantially conductive layer (e.g., a steel base plate) may be coupled to the stimulators to effectively couple the generated stimuli to the bio-printed extracellular matrix.

In at least one embodiment, forming the substrate may include using polymers or composite (bioinks) that are affected by energy provided by one or more simulators. For example, a 3D printed extracellular matrix may be formed while receiving energy from one or more stimulators over time. The 3D bio-printed samples may be formed on a bed using one or more extrusions, additive manufacturing, stereolithography, fused deposit modeling, near field electrospinning, injection molding or any operable combination thereof.

In at least one embodiment, the 3D bioprinted parts may be surface treated using one or more adhesives, atmospheric plasma, laser treatment, solvent bonding or any operable combination thereof that is applied externally with respect to the stimulators that are in the adjustable platform bed 10. In at least one embodiment, a set of conductive layers may be attached to an interface (e.g., base plate 14) between the stimulators and the 3D printed extracellular matrix.

In at least one embodiment, the 3D printed scaffolds may contain one or more cancer cells including, prostate cancer cells and normal cells.

In at least one embodiment, there may be additional stimulators of the same type. For example, the adjustable platform has one mechanical stimulator, two electromagnetic stimulators and two thermal stimulators. However, in an alternative embodiment there may be more than two mechanical stimulators, one, three or more electromagnetic stimulators and/or one, three or more thermal stimulators.

In at least one embodiment, one or more of the stimulators may be used to affect non-invasive cells, invasive cells (e.g., cancer cells), cell size, cell shape, cell location, cell volume, cell growth rate, cell morphology, cell migration speed, cell DNA, cell RNA, cell proteins or any operable combination thereof by providing stimuli over time.

In at least one embodiment, the mechanical stimulator may be used to apply surface treatment through vibration to create structures used for bone mastication, swallowing, and/or parafunctional habits. For example, it has been found that the application of mechanical stimuli in mineralization at etched and bonded dentin interfaces increased mechanical properties at the resin-dentin interface.

In at least one embodiment, electromagnetic stimuli with variable frequency/intensity may be used to eradicate biofilms and membranes. Such electromagnetic stimuli may be used for the non-invasive treatment of prosthetic joint infections.

In at least one embodiment, thermal stimuli may be used to stimulate the bone-like implants. Such thermal stimuli may be used for thermal expansion/contraction of dentinal scaffolds, and/or tubule deformations.

Figure 2A:
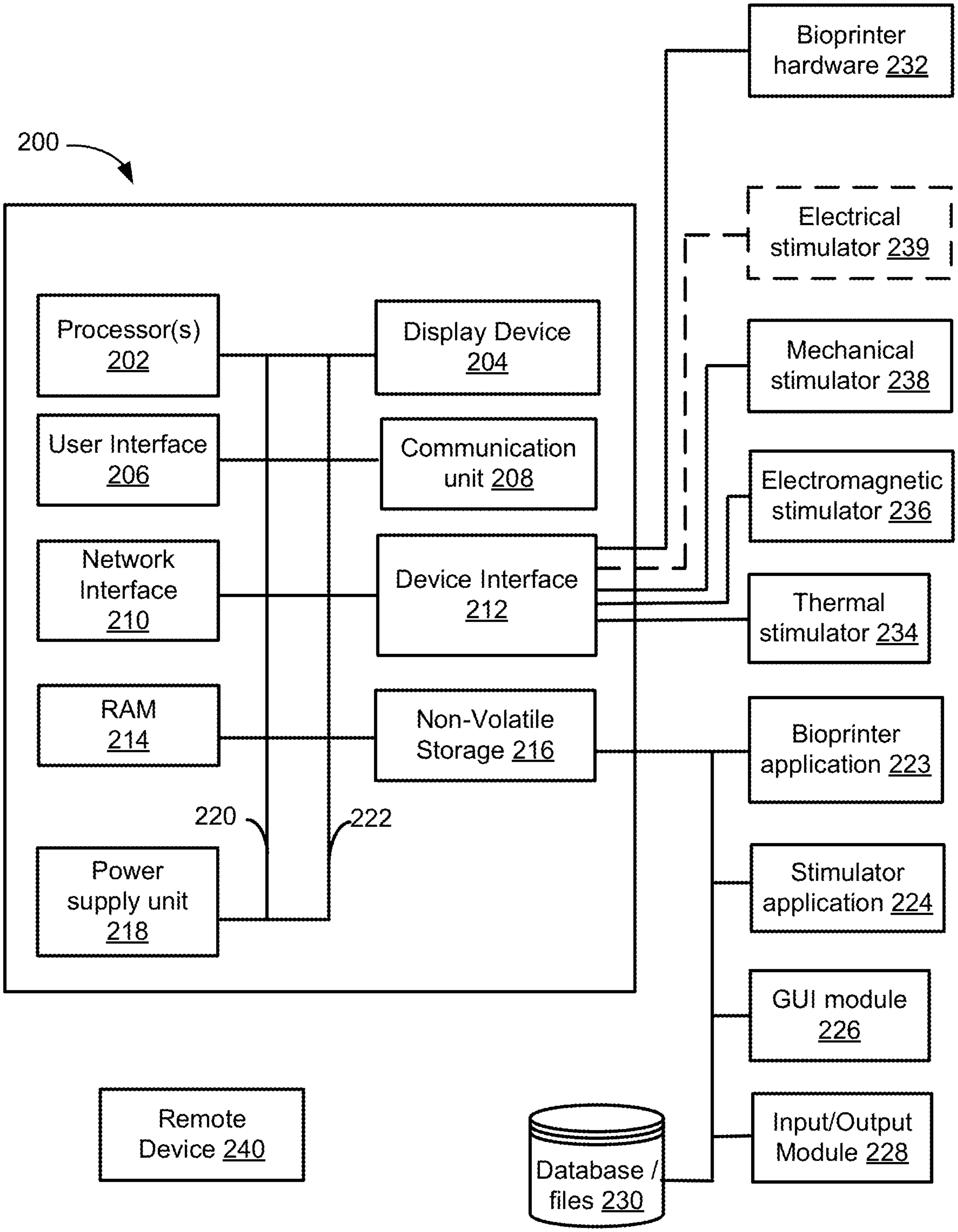
FIG. 2A is a block diagram of an example embodiment of a bioprinter system that can provide functional stimulation.

Referring now to FIG. 2A, shown therein is a diagram of an example embodiment of a bioprinter system 200 that can provide stimulation during and/or after printing of one or more biomaterials. FIG. 2A shows various physical and logical components of an example embodiment of the system 200. A remote device 240 may be used to interact with the bioprinting system 200 and provide input signals for controlling the operation of the bioprinting system 200 as will be described herein. The remote device 240 may be a desktop computer or a mobile device such as a smart phone, a tablet or a laptop.

As shown, the system 200 includes a number of physical and logical components, including one or more processor(s) 202, a display device 204, a user interface 206, a communication unit 208, a network interface 210, a device interface 212, a memory unit including random access memory ("RAM") 214 and non-volatile storage 216, a power supply unit 218, a communication bus 220 and a voltage rails 222. The communication bus 220 enables the processor(s) 202 to communicate with the other components of the system 200. The various elements of the system 200 can receive power from voltage rails 222 that coupled to the power supply unit 218. The non-volatile memory 216 may be used to store various programs and data files such as those used to provide an operating system for the system 200 and software modules that are used perform various functions related to bioprinting and/or applying stimulation such as, but not limited to, a bioprinter application 223, a stimulator application 224, a GUI module 226, an Input/Output module 228, databases and data files 230 as well as other bioprinter hardware 232. Examples of other bioprinter hardware may include various elements known to those skilled in the art that the processor(s) 202 may be in communication with such as, but not limited to, frame sensor(s), door sensor(s) or actuator(s), housing sensor(s), a hydrogel pump, an electrospinning pump, Ultraviolet LEDs, an atmospheric Plasma head, a solenoid valve to control gas flow, a gas sensor, various steeper motors and any operable combination thereof (some of these elements may be optional depending on the design of the bioprinter).

In order to provide stimulation during and/or after bioprinting, the system 200 further includes stimulators which may be housed within a bioprinter functional platform such as bioprinter functional platform 10. The stimulators include a thermal stimulator 234, an electromagnetic stimulator 236, a mechanical stimulator 238, which are each described in further detail with relation to FIGS. 2B-2D. These various stimulators may be physically implemented in a bioprinting adjustable platform such as the platform 10 of FIGS. 1A-1G or the platform 600 of FIGS. 6A-6E. The stimulators may also include an optional electric stimulator 239, which is described in further detail with relation to FIG. 2F and may be provided by the adjustable platform 600 shown in FIGS. 6A-6E.

The processor(s) 202 execute an operating system, and various modules, as described below in greater detail. In embodiments where there are two or more processors, these processors may function in parallel and perform certain functions. The processor(s) 202 execute various software instructions for implementing the operation of the system 200 as well as controlling the stimulators 234 to 238. The processor(s) 202 may be any suitable processors, controllers or digital signal processors that can provide sufficient processing power depending on the configuration and operational requirements of the bioprinting system 200. For example, the processor(s) 202 may include a high-performance processor.

The display device 204 can be any suitable display that provides visual information depending on the configuration of the system 200. For instance, the display device 204 can be a display suitable for a laptop, a tablet or a handheld device such as an LCD-based display and the like. The display device 204 can provide notifications to the user of the system 200 as well as receive instructions and/or commands from the user if the display device 204 is a touchscreen. In some cases, the display device 204 may be used to show one or more GUIs through an Application Programming Interface. A user may then interact with the one or more GUIs for configuring the system 200 to operate in a certain fashion.

The user interface 206 enables a user to provide input via an input device, which may be, for example, any combination of a mouse, a keyboard, a trackpad, a thumbwheel, a trackball, voice recognition, a touchscreen and the like depending on the particular implementation of the system 200. The user interface 206 may also be used to output information to output devices, which may be, for example, any combination of the display device 204, a printer and/or a speaker.

The communication unit 208 may be optional and can be a radio that communicates utilizing CDMA, GSM, GPRS or Bluetooth protocol according to standards such as IEEE 802.11a, 802.11b, 802.11g, or 802.11n. The communication unit 208 can provide the processor(s) 202 with a way of communicating wirelessly with certain components of the system 200 or with other devices or computers that are remote from the system 200.

The network interface 210 permits communication with a network, or other electronic devices and/or servers, which may be remotely located from the system 200 but accessible by some network. The network interface 210 may also include other interfaces that allow the system 200 to communicate with other devices or computers. For example, the network interface 210 may include any combination of an Internet, Local Area Network (LAN), Ethernet, Firewire, modem or digital subscriber line connection.

The device interface 212 can be used to interface with one or more devices; for example, one or more of the stimulators 234 to 238 and certain hardware components of the bioprinter hardware 232. In at least one embodiment, the device interface 212 can include any combination of a serial port, a parallel port or a USB port that provides USB connectivity. In at least one embodiment, the device interface 212 may include a relay board or a multichannel Analog to Digital Converter (ADC) and a multichannel Digital to Analog Converter (DAC) for allowing electrical communication between the processor(s) 202 and the stimulators 234 to 238 so that control signals specifying values for parameters for each of the stimuli may be sent to the stimulators 234 to 238 and any data that is measured by any of the stimulators 234 to 238 may be sent to the processor(s) 202 for analysis. For example, the amplitude and frequency of the electromagnetic, mechanical and electrical stimuli may be provided to the stimulators 236, 238 and 239, respectively, whereas a temperature control signal may be sent to the thermal stimulator 234 and a temperature feedback signal may be received by the device interface 212.

The RAM 214 and the non-volatile storage 216 may be provided in a memory unit or a data store of the system 200. The RAM 214 provides relatively responsive volatile storage to the processor(s) 202. The non-volatile storage 216 stores program instructions, including computer-executable instructions, for implementing the operating system and software modules, as well as storing any data used by these software modules. The data may be stored in database or data files 230, such as for data relating to one or more types of stimuli that may be applied to certain printed biomaterials by the system 200 to affect a certain change in a certain type of printed biomaterial. The database/data files 230 can be used to store data for the system 200 such as system settings, parameter values, and calibration data. The database/data files 230 can also store other data required for the operation of the bioprinter application 223, the stimulator application 224 or the operating system such as dynamically linked libraries and the like.

During operation of the system 200, the software instructions for the operating system, and the software modules, as well as any related data may be retrieved from the non-volatile storage 216 and placed in RAM 214 to facilitate more efficient execution. Other computing structures and data architectures may be used as appropriate.

The power supply unit 218 can be any suitable power source or power conversion hardware that provides power to the various components of the system 200. The power supply unit 218 may be a power adaptor or a rechargeable battery pack depending on the implementation of the system 200 as is known by those skilled in the art. In some cases, the power supply unit 218 may include a surge protector that is connected to a mains power line and a power converter that is connected to the surge protector (both not shown). The surge protector protects the power supply unit 218 from any voltage or current spikes in the mains power line and the power converter converts the power to a lower level that is suitable for use by the various elements of the system 200. In other embodiments, the power supply unit 218 may include other components for providing power or backup power as is known by those skilled in the art.

The stimulator devices 234 to 239 include hardware elements that, under software control, can be used to apply one or more stimuli to printed biomaterials during printing and/or after printing. For example, the thermal stimulator 234 can include one or both of the thermoelectric cells 24*a* and 24*b* or more thermoelectric cells, the electromagnetic stimulator 236 can include one or both of the electromagnetic coils 20*a* and 20*b* or more electromagnetic coils, the mechanical stimulator 238 can include the piezoelectric transducer 22 or two or more mechanical transducers and the electrical stimulator can include contacts shown in FIGS. 6A-6E. An example embodiment for the thermal stimulator 234 is provided in FIG. 2B. An example embodiment of the mechanical stimulator 238 is provided in FIG. 2C. An example embodiment of the electromagnetic stimulator 236 is provided in FIGS. 2D-2E. An example embodiment of the electric stimulator 239 is provided in FIG. 2F.

The system 200 includes a number of software modules/programs with software instructions that are to be executed on the processor(s) 202 for printing biomaterial and/or applying one or more stimuli to printed biomaterial. The software programs that may be executed by the processor(s) 202 include, but are not limited to, the bioprinter application 223, the stimulator application 224, the GUI module 226, and the input/output module 228. It should be noted that in alternative embodiments, the software instructions may be organized in a different manner, i.e., by a different number of software modules, as long as the functionality described herein is provided.

The system 200 executes the software instructions for the bioprinter application 223 to create various types of printed biomaterials as is known to those skilled in the art. The bioprinter application 223 includes program instructions that, when executed by the processor(s) 202, configure the processor(s) 202 to implement one or more methods for allowing a user to create printed biomaterials. For example, the bioprinter application 223 may instruct the processor(s) 202 to execute the software instructions of the GUI module 226 to provide a user interface to allow the user to interact with the bioprinter application 223 so that the processor(s) 202 may receive control inputs and various parameter values and other data to print one or more biomaterial structures. Alternatively, the control inputs may be predefined in software files or provided through communication with another device.

The system 200 executes the software instructions for the stimulator application 224 to apply one or more stimuli during and/or after the printing of one or more biomaterial structures, which may also be referred to as samples or specimens, in some cases. The stimulator application 224 includes program instructions that, when executed by the processor(s) 202, configure the processor(s) 202 to implement one or more methods for allowing a user to apply one or more stimuli to one or more printed biomaterials during printing and/or after printing. The bioprinter application 223 along with the stimulator application 224 may operate together to perform one or more methods such as method 400 shown in FIG. 4, for example. Alternatively, the control inputs for the stimuli may be predefined in software files or provided through communication with another device.

The stimulator application 224 may include program instructions, which may be referred to as stimulation program instructions. The stimulation program instructions, when executed by the processor(s) 202, generates one or more types of stimuli and provides them to the appropriate stimulators 234 to 238 in a particular temporal sequence such as sequentially and/or at the same time (i.e., simultaneously). Any combination of the intensity level (e.g., current and/or voltage amplitude), waveform shape (e.g., pulse width), frequency (e.g., pulse train frequency), number of pulses and overall time duration of the stimuli may be controlled and applied through the stimulator application 224.

The GUI module 226 includes program instructions that, when executed by the processor(s) 202, configure the processor(s) 202 to generate various GUIs that are then displayed on the display device 204, or another visual output device, to display options to the user for performing various functions such as selecting a mode of operation of the bioprinter application 223 and/or the stimulator application 224 and hence control the operation of the system 200. The GUI module 226 also includes software instructions for displaying stimulation results and/or measurement data depending on the mode of operation of the stimulator application 224.

The input/output module 228 includes software instructions that, when executed by the processor(s) 202, configure the processor(s) 202 to store data in the databases/files 230 or retrieve data from the databases/files 230. For example, any input data from the user, such as control inputs (e.g., for selecting a mode of operation), and/or stimulus parameters that is received through one of the GUIs can be stored and/or provided to the processor(s) 202. In addition, any measured data may be provided from the input/output module 228 to the GUI module 226 for display on the display device 204. Alternatively, or in addition thereto, such measured data may be provided by the input/output module 228 to the communication unit 208 or network interface 210 for transmission to another electronic device and/or to a remote storage device.

The remote device 240 can run a remote control software application that the user can use to control the bioprinter system 200 and in particular the bioprinter application 223 and the stimulator application 224. A user may enter their account information (e.g., email and password) to access the main page of the remote control software application. The main page may have three sections including a device control section, a camera display section (for a camera located in the bioprinter device) and/or a user profile section.

The device control section allows the user to connect to the bioprinter system 200 by selecting from a list of available Bluetooth connections that is displayed in the device control section. Before connecting to the bioprinter system 200, the user may wish to turn on the Bluetooth connectivity on the remote device 240 and pair with the bioprinter system 200. After connecting the remote device 240 to the bioprinter system 200, control parameters for the bioprinter system 200 may be displayed on the remote device 240. When the user changes a parameter value, the parameter value may be sent to the bioprinter system 200.

The camera display section of the remote application allows the user to view images that are obtained from a camera that is located inside the chamber of the bioprinter system where the bioprinting is performed. The images from the camera may be shown in the camera display section in real-time. The user may display these images by touching or selecting a camera button. Before displaying the camera images, the data connection between the remote device 240 and the camera within the bioprinter is checked.

The user profile section may include a user name at the top of the section, a logout button which allows the user to log out of their account, and/or device settings. The user profile section may also include device settings which the user may use to control the operation of the bioprinter by adjusting several control inputs such as hydrogel or FDM selection, scaffold type and/or nozzle size. The device settings may also include information on the device type.

The user may also adjust the device settings to control one of more aspects of the stimuli that are generated by the stimulators 234 to 238. For example, the user may set parameters on the bioprinter device to adjust control signals that are sent to the stimulators 234 to 238 where the parameters may include: 1) mechanical stimulation frequency and/or amplitude control, 2) temperature control (e.g., a temperature setting in a temperature range such as about −20 degrees Celsius to about 70 degrees Celsius, for example), 3) two separate EM frequency and amplitude control parameters, and/or 4) electrical waveform, frequency and/or amplitude. In at least one embodiment, other parameters which may be set for the stimuli may include providing two or more stimuli at the same time or sequentially, and/or for each stimulus indicating the amount of time that the stimulus is provided and/or also whether the amplitude of the stimulus is constant or if it the amplitude is varied over time. A stimulus type is defined based on the modality of the stimulus such as whether the stimulus is a mechanical stimulus, an electromagnetic stimulus, a thermal stimulus or an electrical stimulus.

In at least one embodiment, the user may also adjust the device settings to control an operation mode for the bioprinter system. For example, there may be four options to change the status of the bioprinter including: 1) provide mechanical stimulation, 2) provide electromagnetic stimulation, 3) provide thermal stimulation, 4) provide electrical stimulation and 5) provide no stimulation. There may also be an operation mode where two or more of the stimuli may be provided.

In at least one embodiment, when using the remote control software application, all of the input commands and various input parameters that are sent to the bioprinter system 200 may be stored in the memory 216 of the remote device 240. In at least one embodiment, the user may choose to store the input commands and various input parameters on another storage device such as a cloud device.

The transmission of data and control inputs between the remote device 240 and the bioprinter system 200 may employ device security which may be implemented using a REST API (also known as a RESTful API) for Android and iOS platforms. The JSON Web Token or JWT may also be used which is a web standard (RFC 7519) that defines a compact, self-contained method of secure data transmission between different devices through use of a JSON object. The transmitted data can be verified through digital signature. For example, JWTs can be signed by a private key (using the HMAC algorithm which employs a type of message authentication code) or a pair of private and public keys (using the RSA algorithm). The JWT standard creates a private key for each user, which can be a collection of encrypted user information. Therefore, as the user logs in, authentication is performed, and a hash token is created in the system according to the key. The transmitted data may then be exchanged through the verification of this token. Authentication allows the user to send requests, access services, and find resources. If the token has expired or is lost in any way, then the data transmission will be stopped, and the user will have to log in again.

Figure 2B:
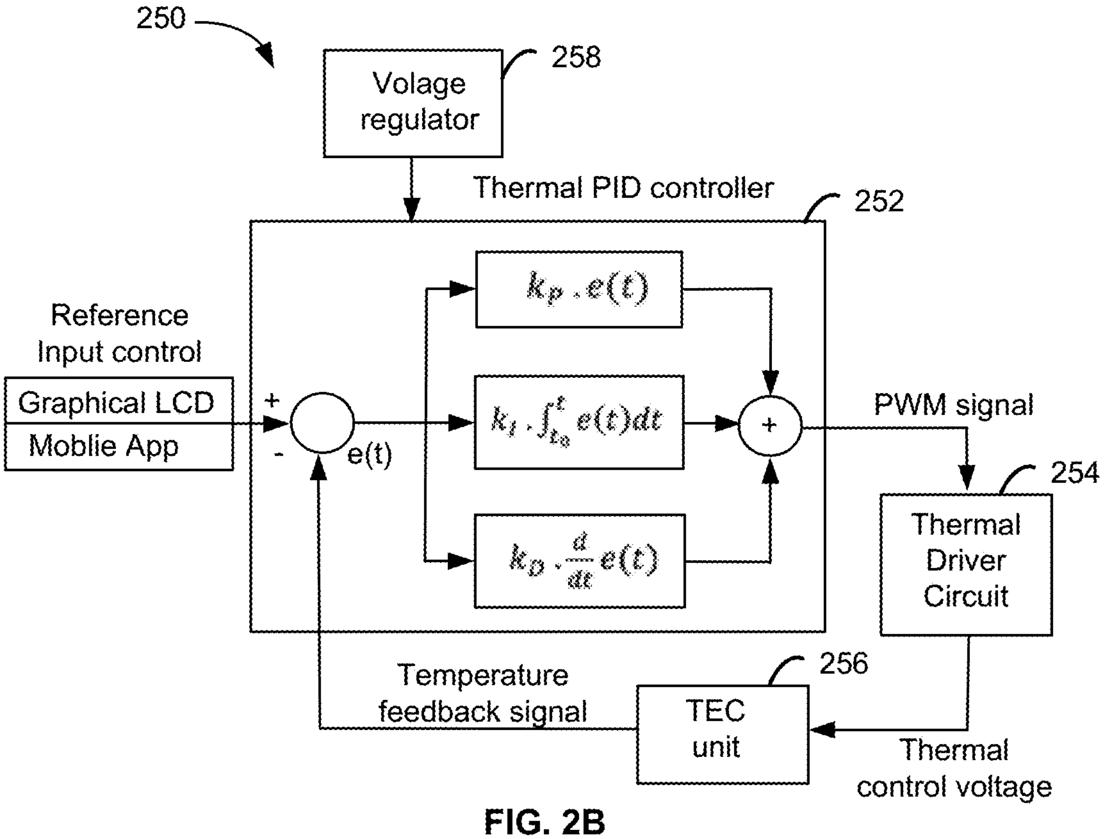
FIG. 2B is a block diagram of an example embodiment of a thermal stimulator.

Referring now to FIG. 2B, shown therein is a block diagram of an example embodiment of a thermal stimulator 250 which includes a thermal controller 252, a thermal driver circuit 254, a thermoelectric cell (TEC) unit 256 and a voltage regulator 258. The controller 252 may be implemented using one of the processor(s) 202 and the functionality of the voltage regulator 258 may be provided by the power supply unit 218. The controller 252 is a thermal PID controller which receives an input control signal for a temperature setting for one or more thermal stimuli and then applies the PID control method via several equations (e.g., as shown in FIG. 2B) to generate a Pulse Width Modulated (PWM) signal that is input to the thermal driver circuit 254. The thermal driver circuit 254 then generates a thermal control voltage that is provided to the TEC unit 256. The TEC unit 256 may be implemented using the elements of platform 10 that are used to generate thermal stimuli and aid with thermal dissipation including at least one of the thermoelectric cells 24*a*, 24*b*, the fan 28, and the heat sink 26. For example, the thermoelectric cells 24*a*, 24*b* may be located under certain regions of the plate 14 for providing thermal stimuli to certain locations of one or more biomaterial structures that are located above the plate 14. In at least one embodiment, one of the thermoelectric cells 24*a*, 24*b* may be used to generate cold thermal stimuli and the other thermoelectric cell may be used to generate hot thermal stimuli. Depending on the implementation of the thermoelectric cells 24*a*, 24*b*, the temperature range for the thermal stimuli may range from about −20 degrees Celsius to about 70 degrees Celsius.

A thermal sensor, such as thermal sensor 30, which may be part of the TEC unit 256 measures the temperature of the thermal stimuli and generates a temperature feedback signal that is provided to the input of the thermal PID controller 252 for comparison with a reference input control value that is used to set a temperature value for the one or more thermal stimuli. The reference input control value may be obtained from the user through an input of the bioprinter system 200 such as a touchscreen or via the remote software application that is operated on the remote device 240, or this may be obtained from files stored in memory 216.

Figure 2C:
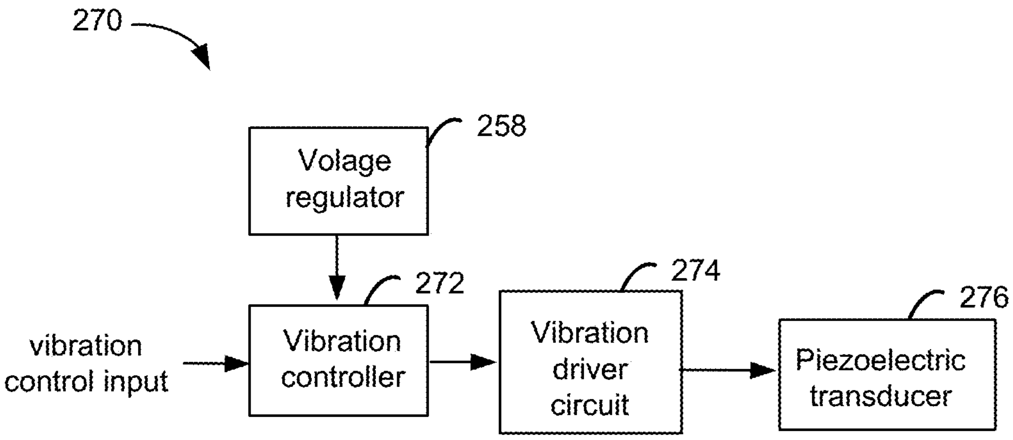
FIG. 2C is a block diagram of an example embodiment of a mechanical stimulator.

Referring now to FIG. 2C, shown therein is a block diagram of an example embodiment of a mechanical stimulator 270 which includes a vibration controller 272, a vibration driver circuit 274, a piezoelectric transducer 276 and a voltage regulator 258. The controller 272 may be implemented using one of the processor(s) 202 and the functionality of the voltage regulator 258 may be provided by the power supply unit 218. The controller 272 receives a vibration control input which may specify the amplitude and frequency of vibration as well as whether the vibration stimuli is to be continuous or intermittent. The vibration controller 272 then generates a corresponding mechanical drive signal that is input to the vibration driver circuit 274. The vibration driver circuit 274 then generates a vibration control signal that is provided to the piezoelectric transducer 276 which generates the one or more mechanical stimuli. In alternative embodiments, there may be multiple piezoelectric transducers 276 that are used and so there may be more than one vibration driver circuit 274 in those cases.

The vibration control input may be obtained from the user through an input of the bioprinter system 200 such as a touchscreen or via the remote software application that is operated on the remote device 240. The frequency specified in the vibration control input will affect the speed of vibration of the piezoelectric transducer 276 and increasing the frequency may cause the piezoelectric transducer 276 to vibrate the base plate 14 of the bioprinter functional platform 10 with more force up to a certain point. The optimal frequency of mechanical stimulation may be determined experimentally for inducing the desired cellular response since the mechanical frequency depends on several factors including the stiffness of the substrate, and the size of the cells. Both constant and pulsed signals may be used to drive the piezoelectric transducer 276, which corresponds to either continuous (vibration control) or intermittent (position control) modes of operation. For example, a piezoelectric transducer may be used to control the position of a microfluidic channel in a bioprinted material with sub-micron accuracy. The amplitude of the signal provided to the piezoelectric transducer 276 may range from about 0 V to about 5 V. The vibration frequency may also be selected based on a desired effect on the printed biomaterial. For example, the frequency which may be used for cell proliferation may range from about 0 Hz to about 100 Hz.

Figure 2D:
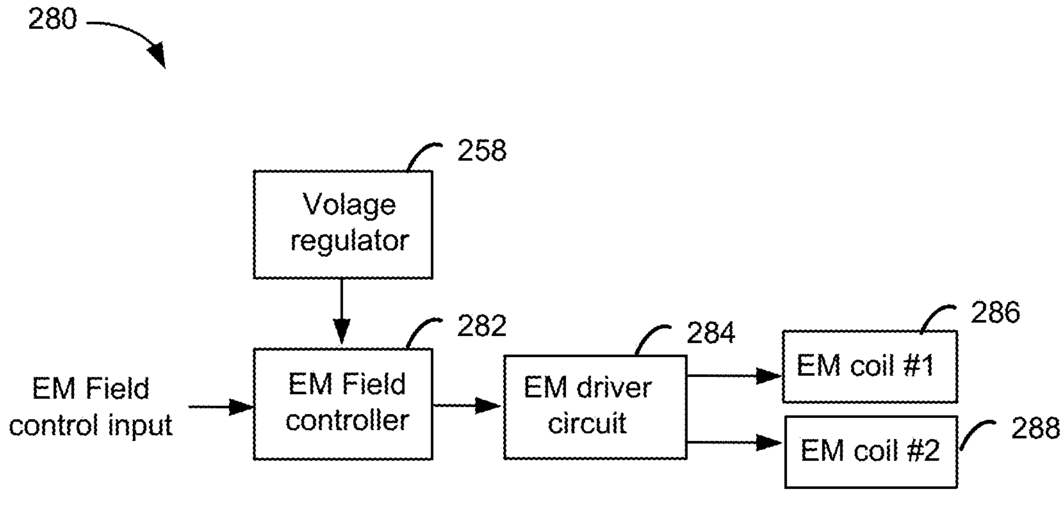
FIG. 2D is a block diagram of an example embodiment of an electromagnetic stimulator.

Referring now to FIG. 2D, shown therein is a block diagram of an example embodiment of an electromagnetic stimulator 280. The electromagnetic stimulator 280 includes an electromagnetic field controller 282, an EM driver circuit 284, a first EM coil 286 and a second EM coil 288 as well as a voltage regulator 258. The EM field controller 282 may be implemented using one of the processor(s) 202 and the functionality of the voltage regulator 258 may be provided by the power supply unit 218.

The applied voltage may be adjustable on both ends of the magnet coils to control the generated EM field strength. In at least one embodiment, this may be done by using analog power supplies or a PWM method. In addition, or in at least one alternative embodiment, a separate microcontroller may be used to generate a PWM signal with a variable frequency. For example, the ATmega16 microcontroller may be used which has an ADC, USART protocol features, and several separate Timer/Counter units. The input voltage of the ATmega16 microcontroller may be between 7.5 V and 15 V. The ATmega16 microcontroller may be powered by a 5-volt regulator.

Figure 2E:
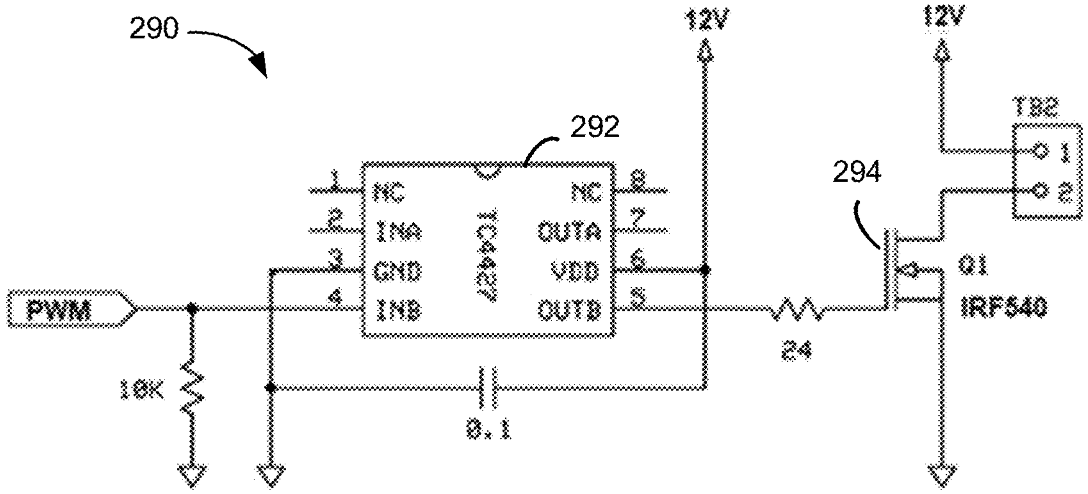
FIG. 2E is a circuit diagram of a portion of an EM driver circuit which may be used with the electromagnetic stimulator of FIG. 2D.

Referring now to FIG. 2E shown therein is a circuit diagram of a portion of an EM driver circuit 290 which may be used with the electromagnetic stimulator 280. The EM driver circuit 290 includes a power transistor, which may be the MOSFET IRF540, which is used to drive the electromagnetic coils. The MOSFET IRF540 can operate up to 100 V and 28 amps. An intermediate circuit between the ATmega16 microcontroller and the power transistor may be used to run the MOSFET power supply. The intermediate circuit may be the TC4427 driver 292.

The amplitude of the EM stimuli may be selected based on the inductance of the electromagnetic coils 20*a*, 20*b* and the desired effect on the printed biomaterials. For example, the electromagnetic coils 20*a*, 20*b* may have an inductance 3.27±0.04 μH. The frequency of the EM stimuli may also be selected based on the desired effect on printed biomaterials. For example, the frequency may be in the range of about 0 Hz to about 100 Hz to effect cell proliferation in the printed biomaterials. To influence magnetic iron oxide nanoparticles (MIONs) that may be in the printed biomaterial, the frequency may be selected in the range of about 400 kHz to about 1.1 MHz.

Figure 2F:
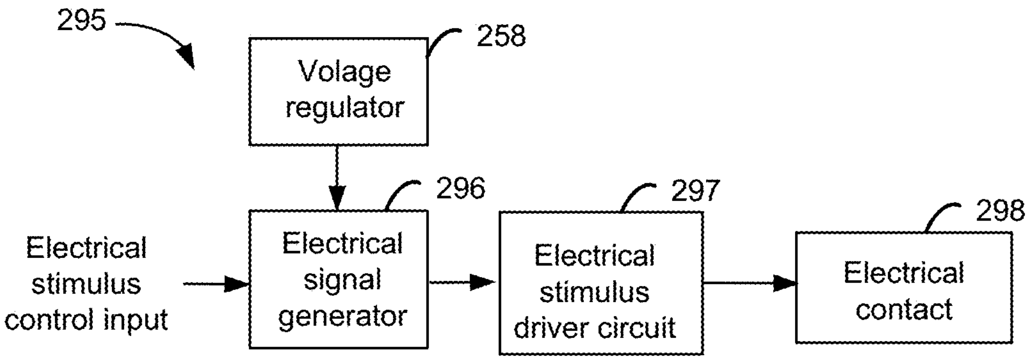
FIG. 2F is a block diagram of an example embodiment of an electrical stimulator.

Referring now to FIG. 2F, shown therein is a block diagram of an example embodiment of an electrical stimulator 295 which includes an electric signal controller 296, an electrical signal driver circuit 297, an electrical contact 298 and a voltage regulator 258. The electric signal generator 296 may be implemented using one of the processor(s) 202, or other hardware as is known by those skilled in the art, and the functionality of the voltage regulator 258 may be provided by the power supply unit 218. The electric signal generator 296 receives an electrical stimulus control input which may specify the type of waveform, amplitude and frequency for the electrical stimulus as well as whether the electrical stimulus is to be continuous or intermittent. The electric signal generator 296 then generates a corresponding electrical drive signal that is input to the electrical stimulus driver circuit 274, which may provide amplification and/or filtering. The output of the electrical stimulus driver circuit 274 is the electrical stimulus that is provided to the electrical contact 298. In alternative embodiments, there may be multiple electrical contacts 298 that are used and so there may be more than one electrical stimulus driver circuit 297 in those cases.

Referring now to FIGS. 3A-3E, shown therein are front perspective, front, side, bottom, and top views of the mechanical assembly 300 and frame 302 for various components of a bioprinter system, such as bioprinter system 200, including the bioprinting platform of FIGS. 1A-1G. The mechanical assembly 300 includes rails 306*a* and 306*b* upon which the adjustable platform 304 is movably coupled so that it may be moved closer to or farther away to a 3D printing head 301 in the horizontal dimension. The adjustable platform 304 may be implemented similarly to the adjustable platform 10 or the adjustable platform 600. A petri dish 318 may be placed on the bed of the adjustable platform 10. The adjustable platform 304 may include clips 304*a*, 304*b* for holding the plate in place. The 3D printing head 301 may be translated up and down as well as from left to right via motors 321*a*, 321*b*.

To provide the moveable coupling of the adjustable platform 304 to the frame 302, the mechanical assembly 300 includes the guide rails 306*a* and 306*b* that are located under the adjustable platform 304 near opposite ends of the adjustable platform 304 and a lead screw 312 that is located under the adjustable platform 304 along a central axis thereof. The guide rails may be implemented using smooth steel rods. The guide rails 306*a* and 306*b* are coupled to a front portion of the frame 302 via brackets 310*a* and 310*b* and are similarly coupled to a rear portion of the frame 302. The guide rails 306*a* and 306*b* also run through slide bushings 308*a*, 308*b* and 309*a*, 309*b*, respectively, which may be linear motion ball bearing slide bushings, that are attached to the bottom of the adjustable platform to allow the adjustable platform 304 to slide along the guide rails 306*a* and 306*b* when it is moved. The lead screw 312 is inserted through a worm gear sleeve 314 and rotatably coupled at either end to the front and rear portions of the frame 302 via brackets (only bracket 316 near the rear portion of the frame 302 is visible). One end of the lead screw 312 is coupled to a motor 320 which turns the lead screw during use so that the adjustable platform 304 is moved closer to or further away from the 3D printing head 301 (this may be referred to as movement along the 3D printer z-axis). The 3D printing head 301 is movably coupled to the frame 302 and may be moved using one or more of the motors 321*a*, 321*b*.

Figure 3A:
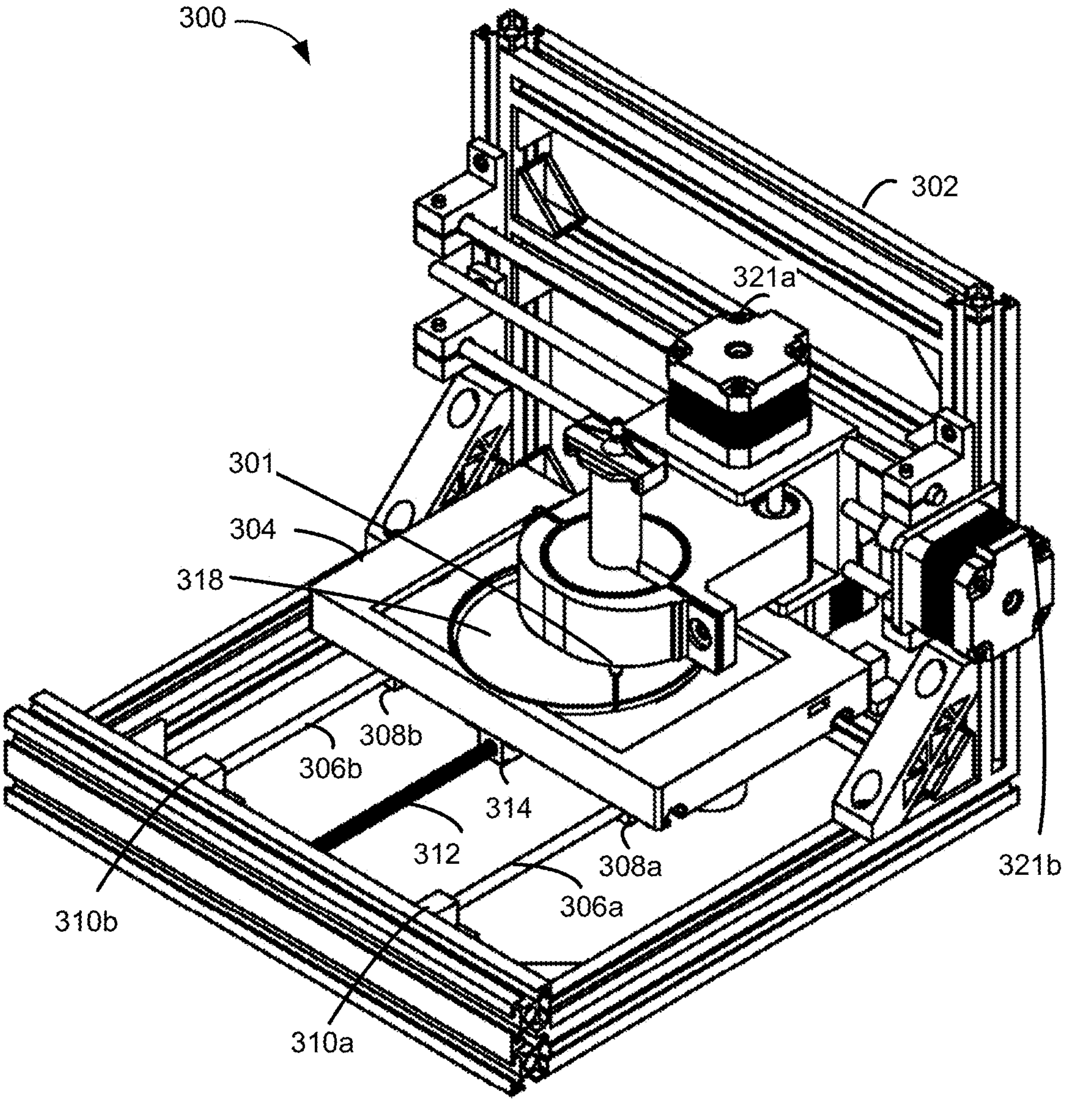
FIGS. 3A-3E are front perspective, front, side, bottom, and top views of the mechanical assembly and frame for various components of a bioprinter system including an adjustable platform bed in accordance with the teachings herein.
Figure 3B:
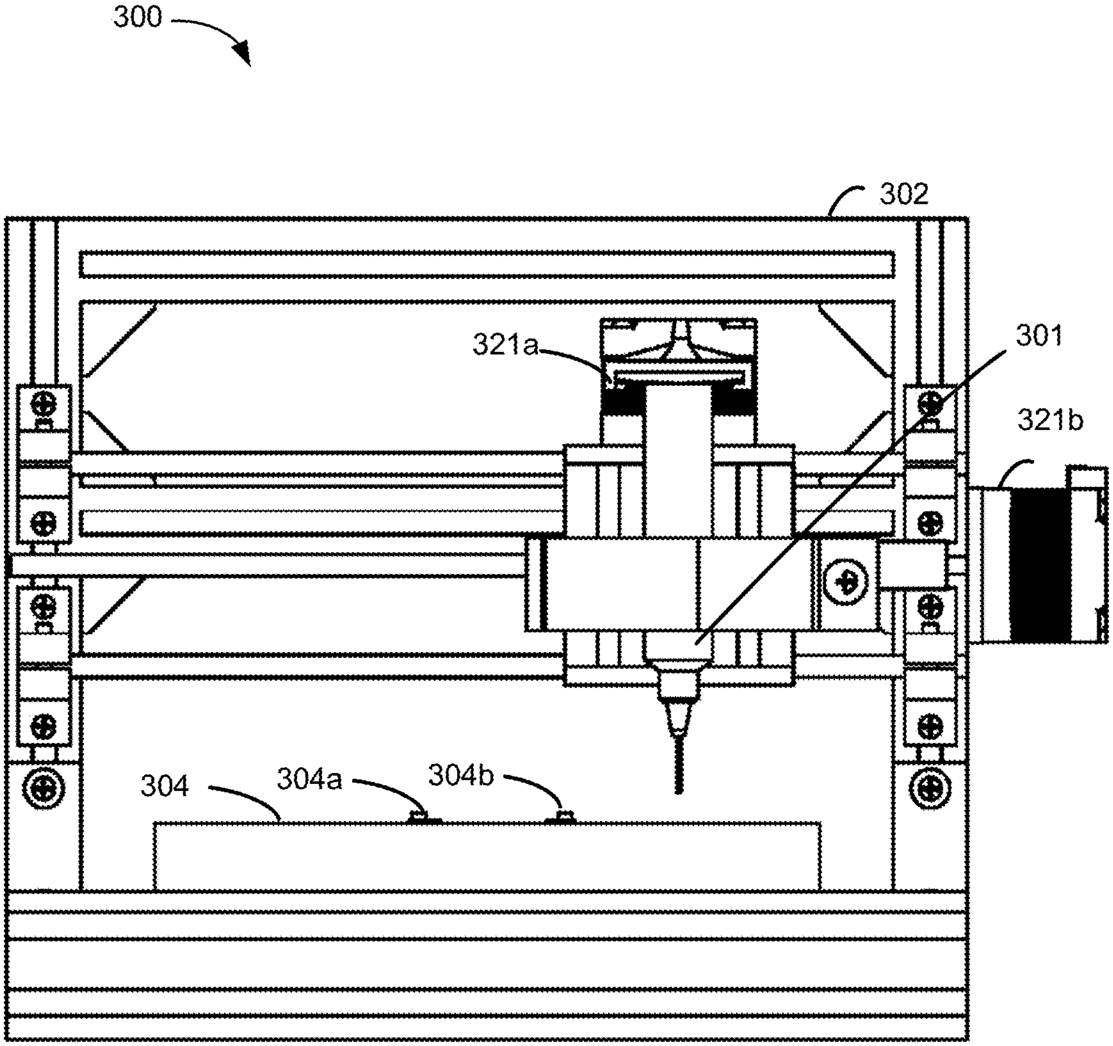
Figure 3C:
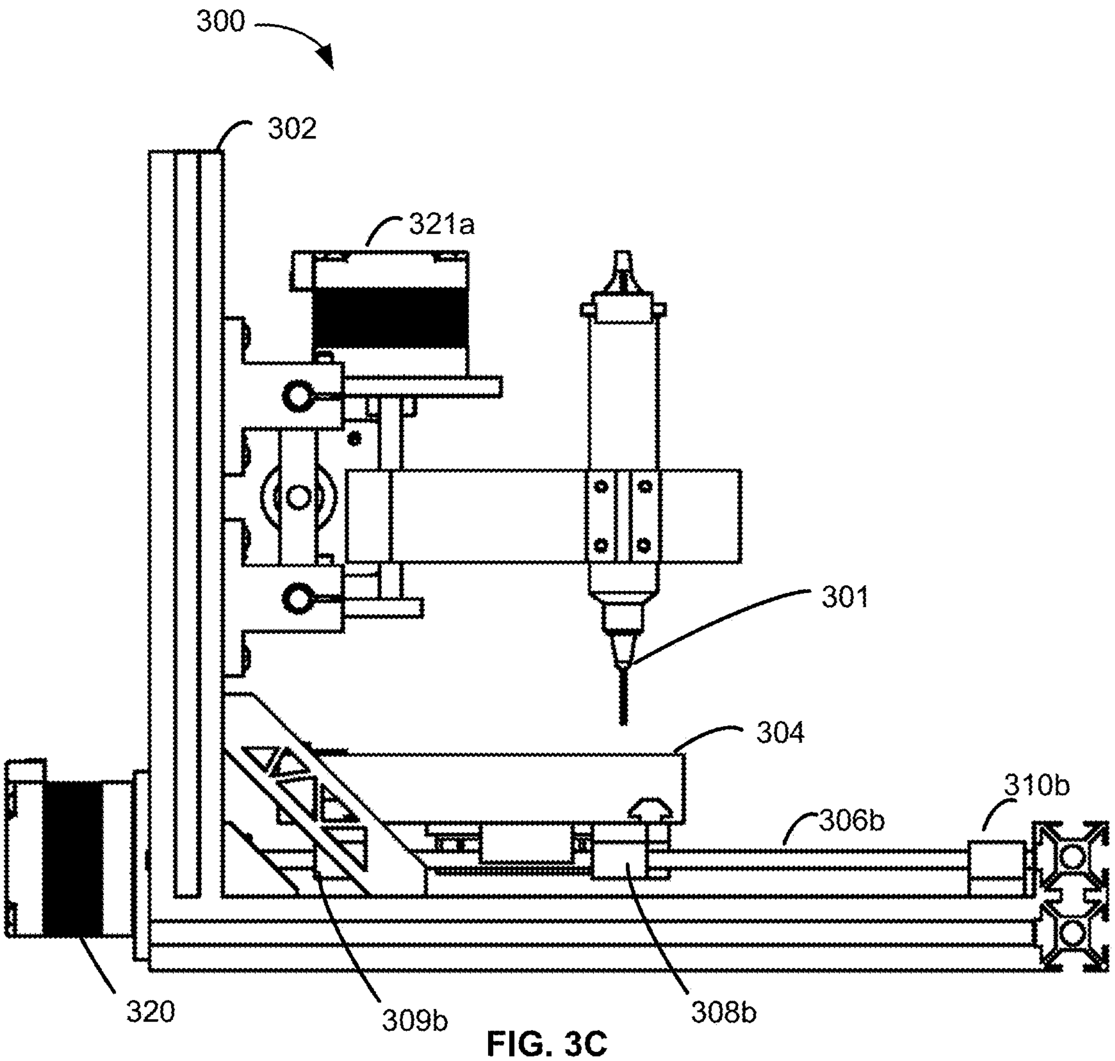
Figure 3D:
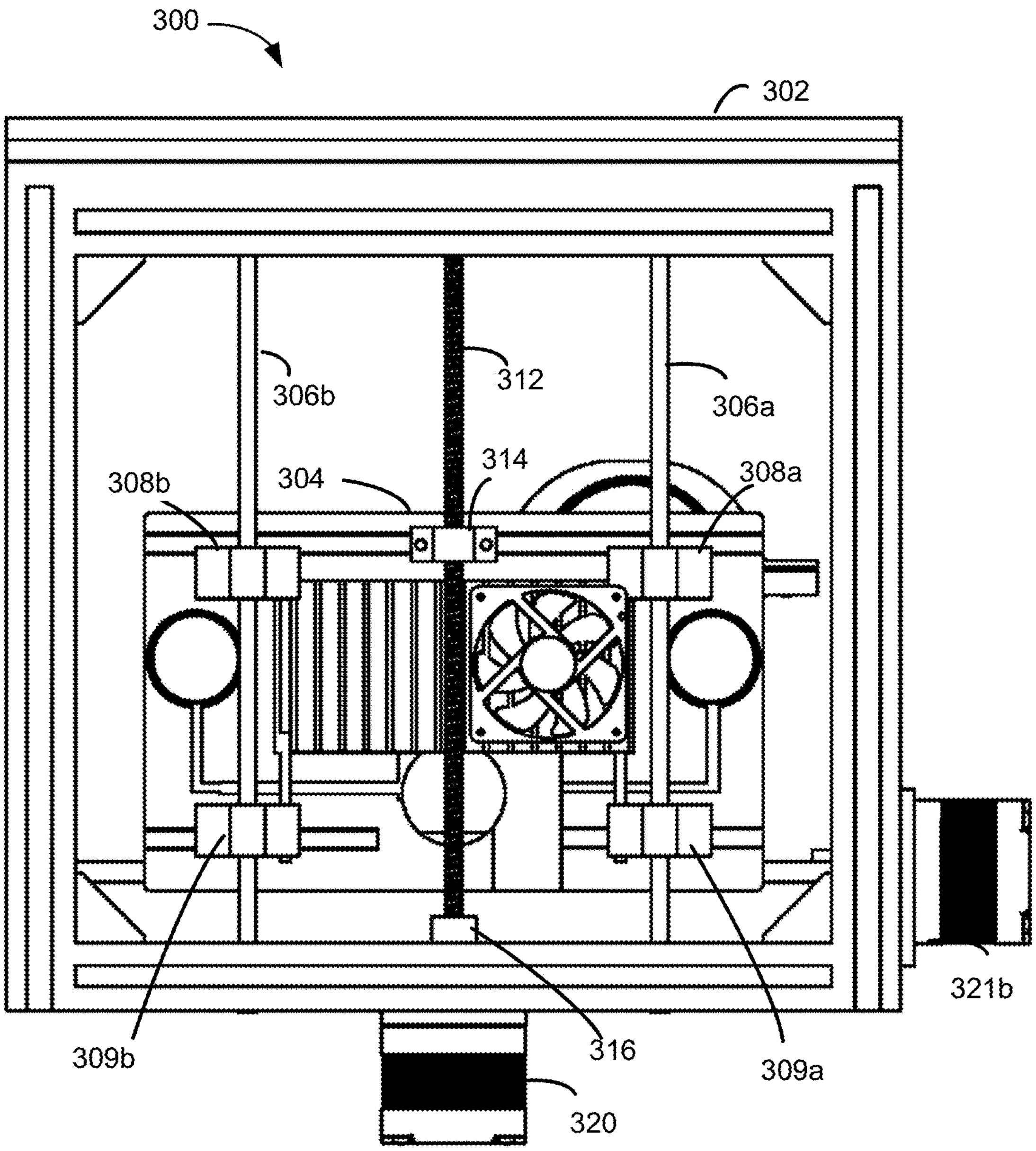
Figure 3E:
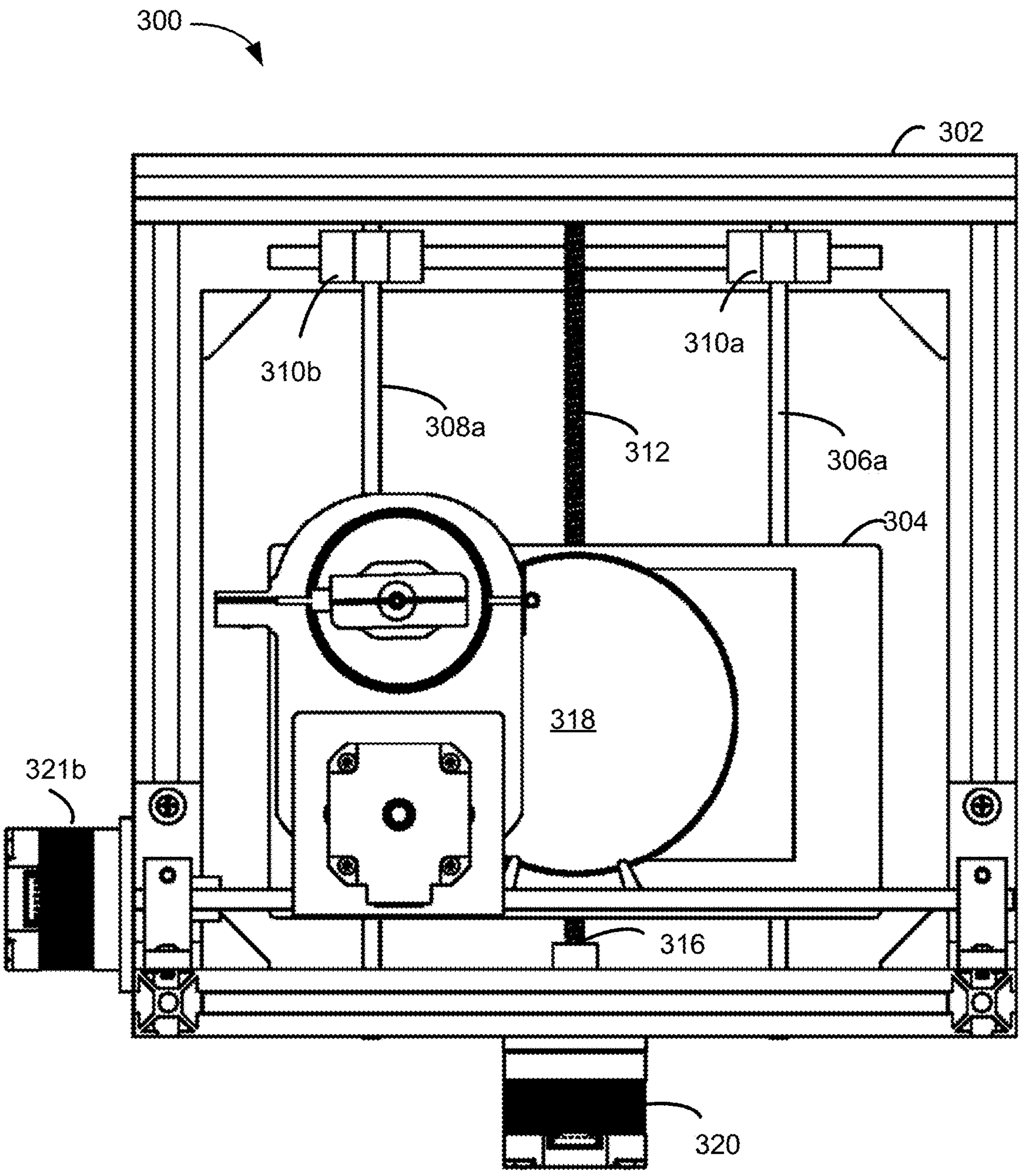
Figure 3F:
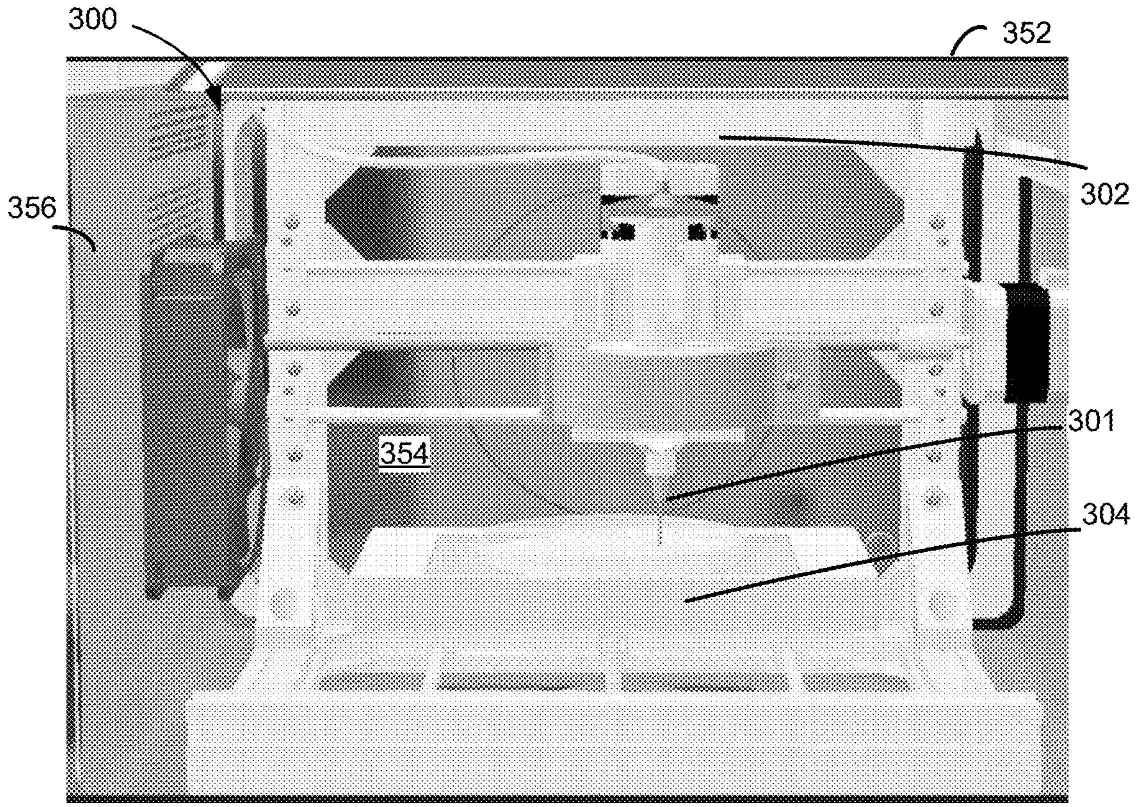
FIG. 3F shows an example of the mechanical assembly and frame of FIGS. 3A-3E installed within a housing that has a bioprinter chamber and a door.

Referring now to FIG. 3F, shown therein is an example of the mechanical assembly 300 and frame 302 installed within a housing 352 that has an internal space that forms a bioprinter chamber 354 and a door 356 which may be closed so to seal the bioprinter chamber 354 during use. The bioprinter chamber 354 may be known as an incubator chamber.

Figure 3G:
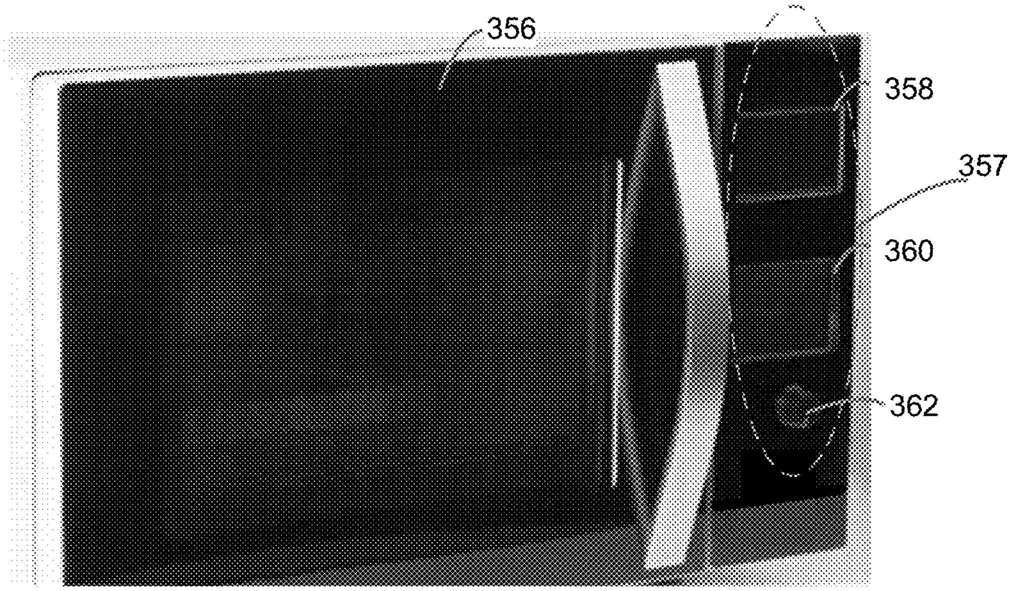
FIG. 3G shows a front view of an example embodiment of the door of FIG. 3F having a control panel for the bioprinter of FIG. 3F.

Referring now to FIG. 3G, shown therein is a front view of an example embodiment of the door 356 having a control panel 357 for the bioprinter of FIG. 3F. A first portion of the control panel 357 is a touch screen 358 that allows a user to enter values for the control parameters for the bioprinter as well as the smart adjustable platform 304. A second portion of the control panel 357 is a touch screen 360 that allows the user to enter values for the 3D printing movement. A third portion of the control panel 357 is a touch screen that allows the user to adjust the size of input values.

Figure 4:
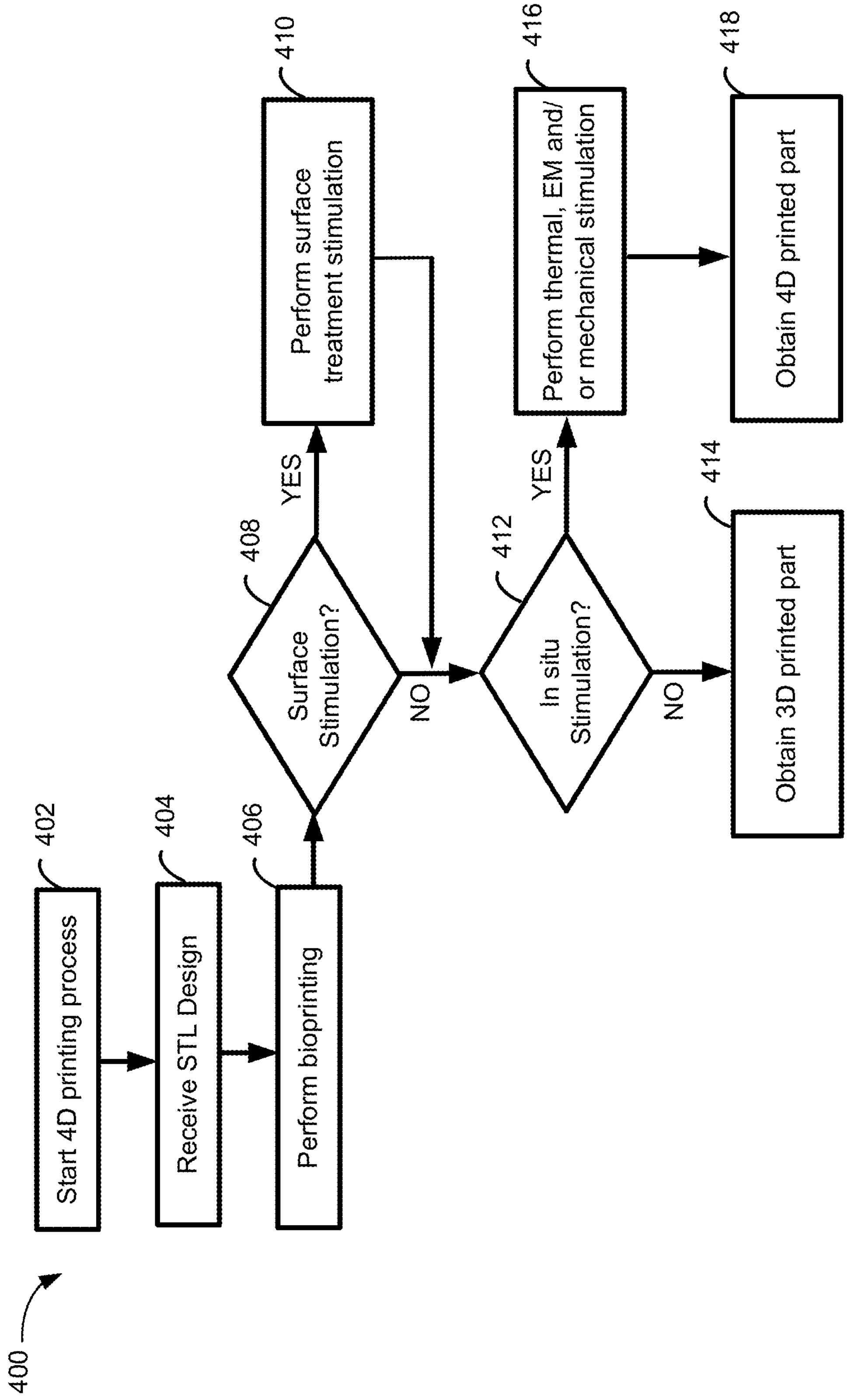
FIG. 4 is a flow chart of an example embodiment of a method for performing in situ stimulation with bioprinting in accordance with the teachings herein.

Referring now to FIG. 4, shown therein is a flow chart of an example embodiment of a method 400 for performing functional stimulation during and/or after bioprinting in accordance with the teachings herein. For ease of illustration, the method 400 is described as being performed using the bioprinting system 200 and by executing various software instructions using the processor(s) 202, for example. However, the method 400 may be used with other bioprinters having an adjustable platform as described herein. At step 402, the 4D bioprinting process 400 is started by initiating the bioprinter system 200 for operation. At step 404, an STL design is received which specifies the parameters that are used for printing one or more biomaterial structures. At step 406, the bioprinting is performed.

The method 400 proceeds to step 408, in which surface stimulation may be applied during and/or after bioprinting. If surface stimulation is selected, the method 400 moves to step 410 where surface treatment stimulation is performed. The surface stimulation may be applied when the bioprinter has components that may provide atmospheric plasma, external low power laser, and/or external photo cure stimulation. An example of this is described in PCT published patent application WO2019180749, entitled "Automatic Additive Multi Stage Portable Three Dimensional Device for Manufacturing of Hard and Soft Organs". Alternatively, or in addition to the plasma, laser or photo curing, surface treatment may be performed by using mechanical stimuli provided by the adjustable smart bed as described herein.

If surface treatment was not selected or at the end of surface treatment, the method 400 moves to step 412, where it is determined whether in situ simulation should be performed based on user input. If the decision is true, then the method 400 moves to step 416 where in situ stimulation is performed. This may involve applying only one type of stimuli (e.g., mechanical, thermal, electrical or electromagnetic) or it may involve applying two or more types of stimuli such as mechanical and thermal stimuli; mechanical and electromagnetic stimuli; thermal and electromagnetic stimuli; mechanical and electrical stimuli; thermal and electrical stimuli; electromagnetic and electrical stimuli; mechanical, thermal and electromagnetic stimuli; mechanical, thermal and electric stimuli; or mechanical, electric, and electromagnetic stimuli or electric, thermal and electromagnetic stimuli. When two or more stimuli are selected they may be provided sequentially or in parallel as described herein. At the end of step 416, a 4D printed part (e.g., one or more biomaterial structures) is obtained at step 418.

Alternatively, if in situ stimulation is not selected at step 412 then the method 400 moves to step 414 where a 3D printed part is obtained.

Figure 5:
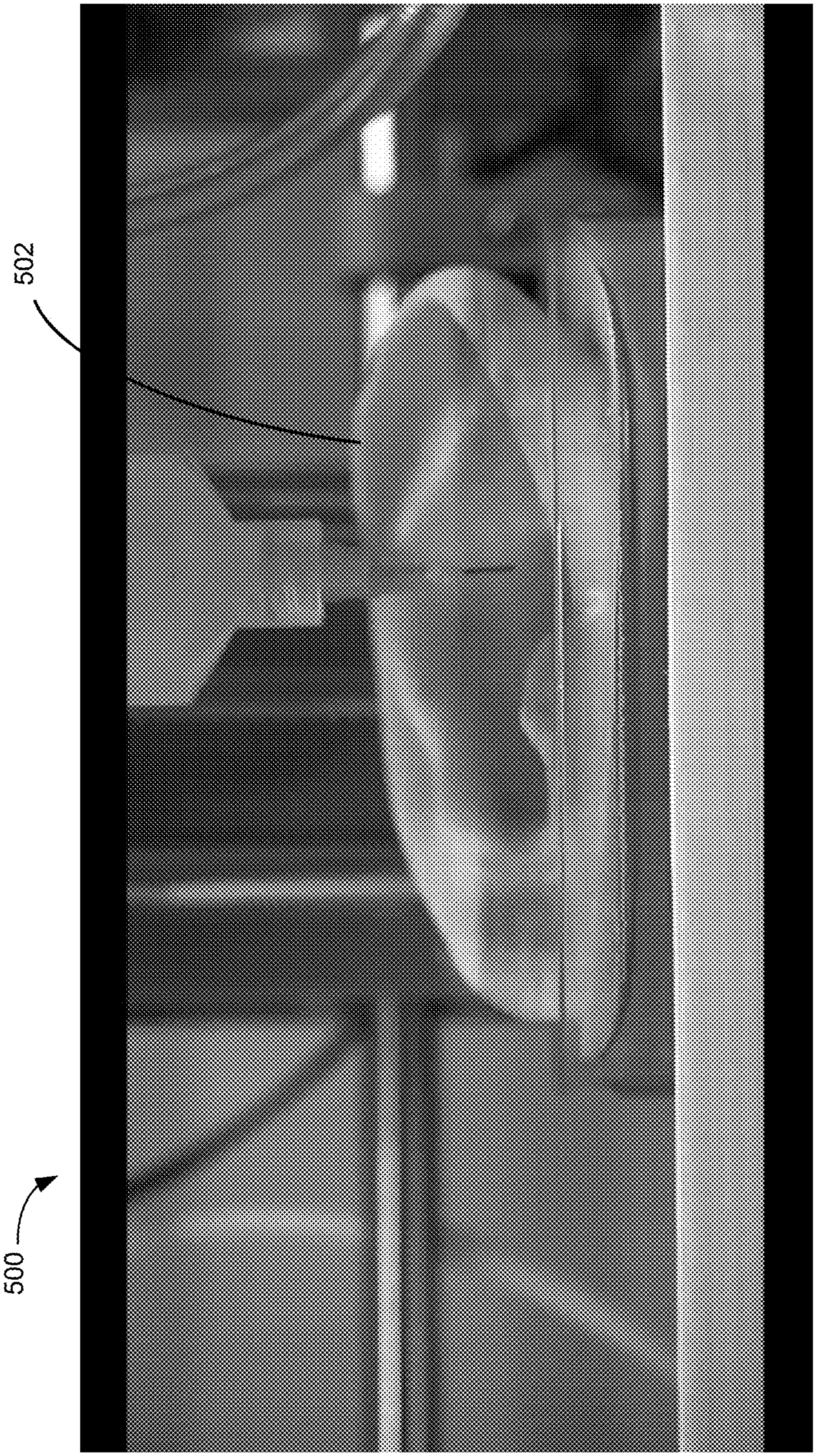
FIG. 5 is an example image of a biomaterial produced by an embodiment of a bioprinter system that has an adjustable platform bed.
Figure 6B:
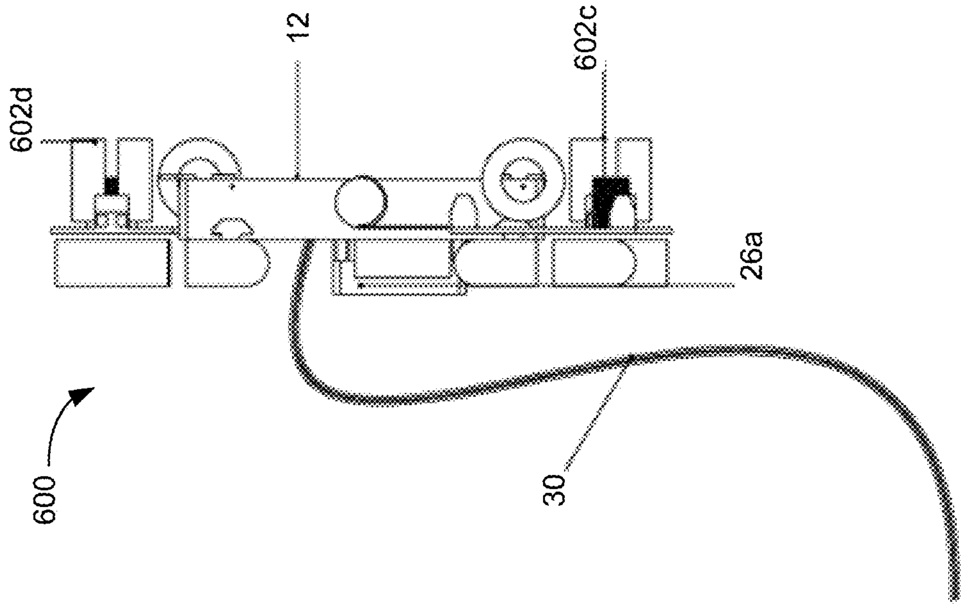
FIGS. 6A-6E are bottom, side, front, top and perspective views, respectively, of another example embodiment of an adjustable platform that can provide in situ stimulation for 4D bioprinting in accordance with the teachings herein.
Figure 6A:
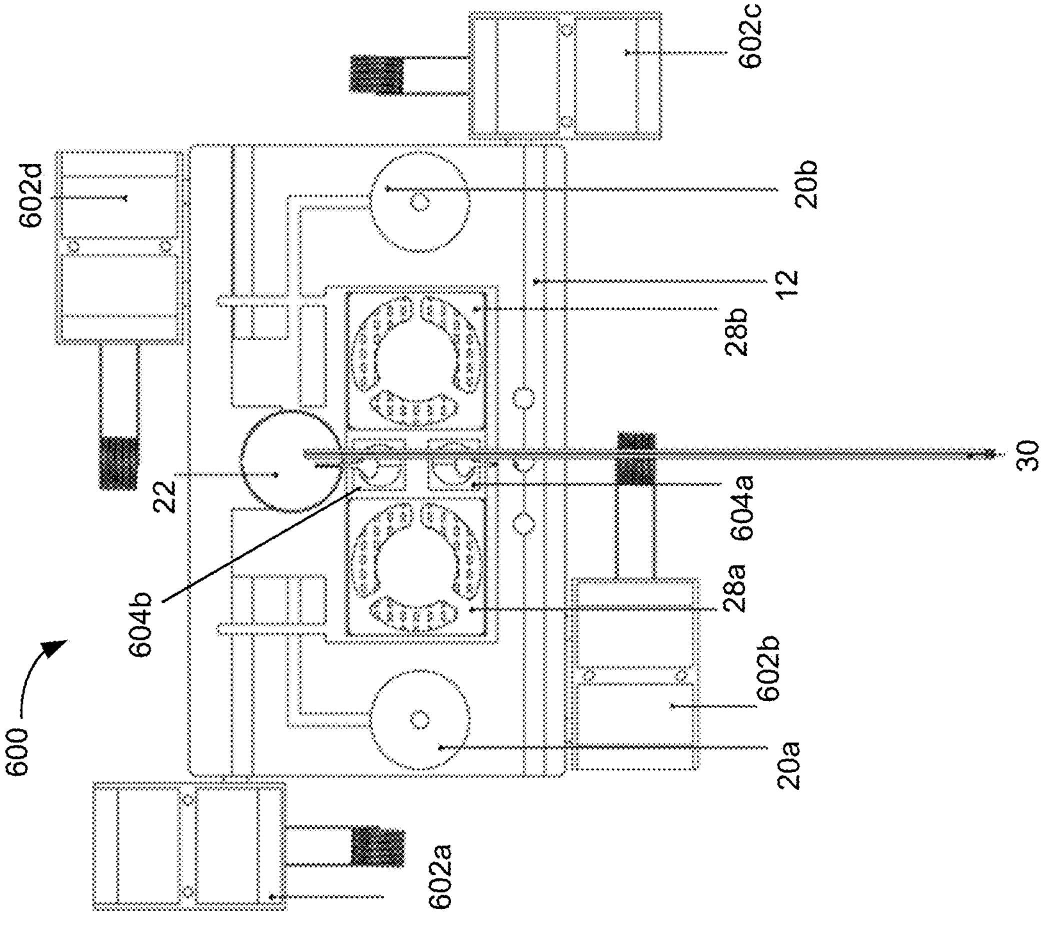
Figure 6C:
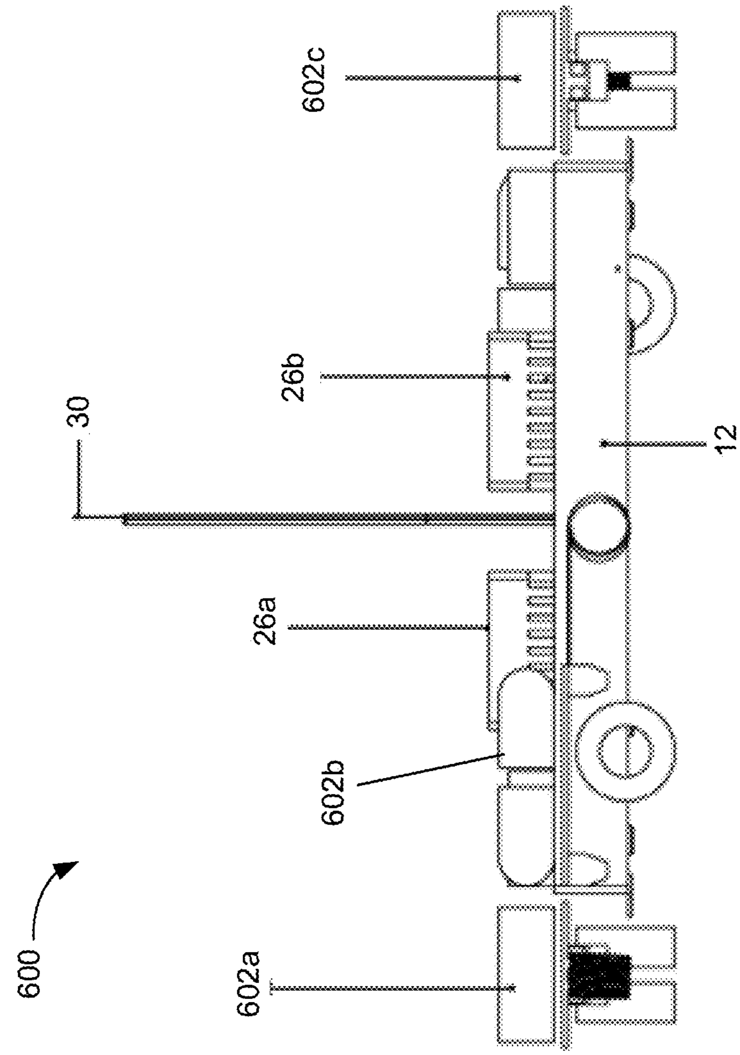
Figure 6D:
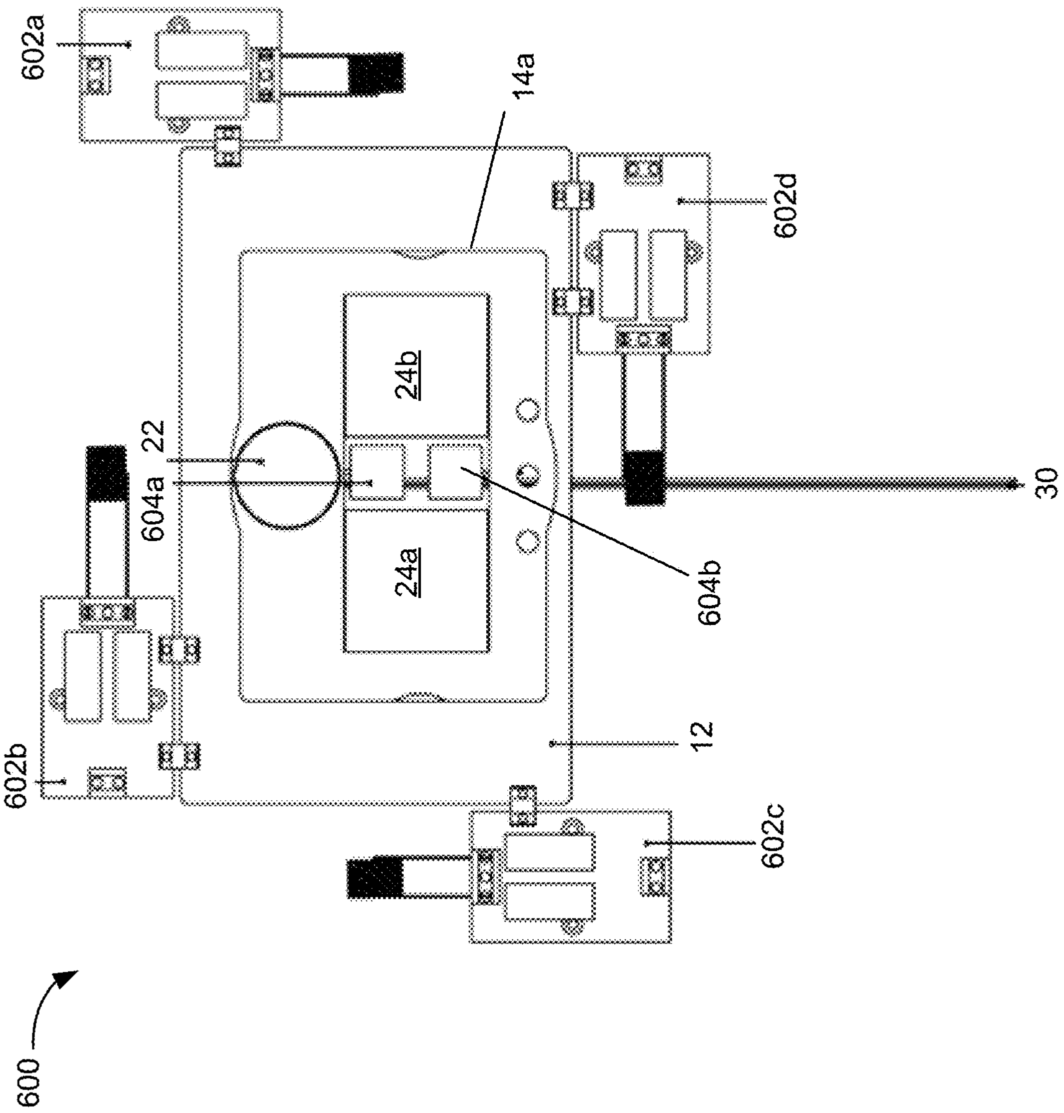
Figure 6E:
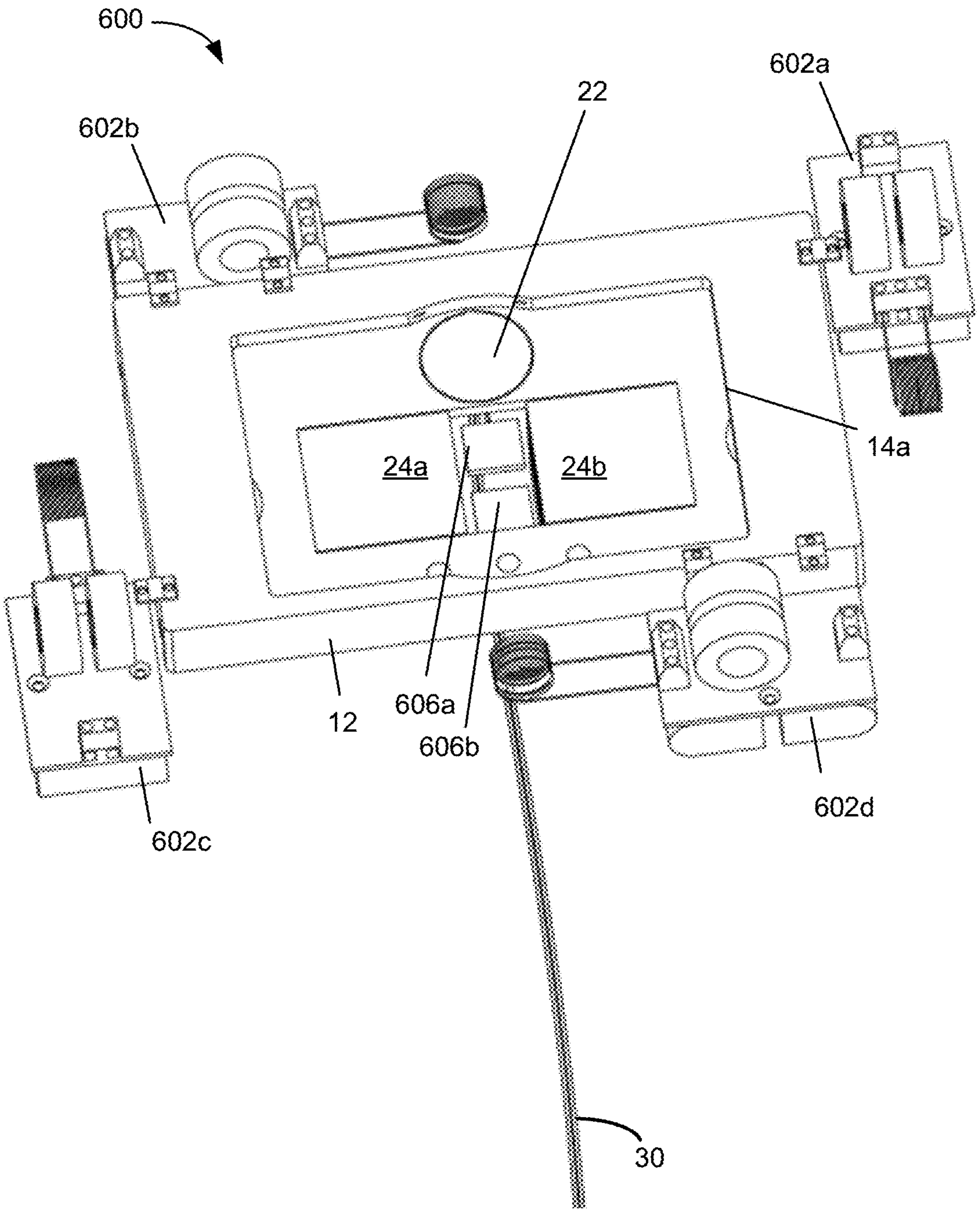

Referring now to FIG. 5, shown therein is an example image of a biomaterial sample 502 produced by an embodiment of a bioprinter system 500 in accordance with the teachings herein. The biomaterial sample is an ear that is bio-printed with cartilage bioink and plasma surface treatment is applied for more cell proliferation.

Referring now to FIGS. 6A-6E, shown therein are bottom, side, front, top and perspective views, respectively, of another example embodiment of an adjustable platform 600 that can provide in situ stimulation for 4D bioprinting in accordance with the teachings herein. The adjustable platform 600 is similar to the adjustable platform 10. Accordingly, similar elements are shown with similar reference numerals. However, the adjustable platform 600 includes additional stimulators including additional electromagnetic coils 602*a*-602*d*, and electrical stimulators 604*a*, 604*b*. The electromagnetic coils 602*a*-602*d* may be high frequency electromagnetic coils. The base plate 14 is not shown in FIGS. 6A-6E for ease of illustration of components that would be covered by the base plate during use, but it should be understood that the base plate 14 covers the area 14*a* shown in FIGS. 6D-6E.

As shown, there are additional electromagnetic stimulators 602*a*-602*d* that are included with the adjustable platform 600 so that EM fields with different orientations can be provided. For instance, the electromagnetic stimulators 602*a*-602*d* can generate high frequency induction EM fields in the XY plane due to their orientation since opposing electromagnetic stimulators 602*a* and 602*c* have the location of their North-South poles reversed compared to one another, opposing electromagnetic stimulators 602*b* and 602*d* have the orientation of their North-South poles reversed, and each of the electromagnetic stimulators 602*a*-602*d* are oriented such that the axis of their electromagnetic coils are in the XY plane. In contrast, the electromagnetic coils 26*a* and 26*b* are oriented to generate EM fields in the Z direction. Accordingly, all of the EM stimulators 26*a*, 26*b* and 602*a*-602*d*, may be used to generate more complex 3D EM fields as EM stimuli where the resulting high frequency EM field will depend on the relative orientation and distance between the various electromagnetic stimulators. The use of high frequency for the EM field may cause a rapid change in the EM field, which induces eddy currents in the printed biomaterial (e.g., tissue) being treated. For example, the eddy currents generate heat due to the resistance of the tissue, which can raise the temperature of the tissue and induce hyperthermia. The EM stimulators 602*a*-602*d* may be implemented using ZVS-based converters, for example, although some EM interference techniques may need to be used as is known by those skilled in the art for operation at certain frequencies.

The new EM stimulators 602*a*-602*d* may be used in various applications such as, but not limited to, changing at least one property of a biomaterial that is printed on the base plate or for studying the use of hyperthermia for cancer drug discovery and developments by treatment based on heat, induced by magnetic nanoparticles, such as in 3D bioprinted scaffolds, for example. In this application, the EM stimulators 602*a*-602*d* may be used to generate EM fields that cause the magnetic nanoparticle (MNP) to move and generate heat. More particularly, in MNP treatment, magnetic nanoparticles are injected into the tumor or cancerous tissue, and an alternating magnetic field is applied to the area, causing the magnetic nanoparticles to oscillate and generate heat through Brownian motion. The addition of heat to this process can increase the efficiency of the MNP hyperthermia treatment. By applying heat to the area, the blood vessels surrounding a tumor can dilate, allowing for greater blood flow and better distribution of the magnetic nanoparticles. This, in turn, can improve the efficacy of the treatment by allowing for more targeted and efficient heating of the cancerous tissue. By applying an EM field, the magnetic nanoparticles can be more effectively directed to the target area, increasing the concentration of the nanoparticles in the cancerous tissue and reducing the risk of damage to surrounding healthy tissue. In this application, the EM field may have a frequency of about 200 kHz to about 1 MHz and the intensity of the EM field can be varied from 0 to 100% of full amplitude.

As shown, the electrical stimulators 604*a*, 604*b* include electrodes. In such cases, the base plate may have conductive regions and insulated regions such that the conductive regions are coupled to the electrodes 604*a*, 604*b* to provide electrical stimulation to certain regions of the base plate where one or more printed biomaterial structures may be located. The electrodes may be implemented using Transcutaneous Electrical Nerve Stimulation (TENS) electrodes or other suitable electrodes. In at least one embodiment there may just be one electrode. Alternatively, in at least one embodiment there may be more than one electrode. Therefore, the adjustable platform may have at least one electrical stimulator with at least one electrode.

The electrical stimulators 604*a*, 604*b* may be used in various applications such as, but not limited to, changing at least one property of a biomaterial that is printed on the base plate. The electrical stimulus provided by the electrical stimulators 604*a*, 604*b* are selected to have desired amplitude, frequencies and waveform. For example, the electrical stimulus may be provided through low-frequency, pulsed electrical currents, which may be applied for various purposes such as applying therapy to a bioprinted scaffold for tissue regeneration and/or to reduce nociceptor cell activity.

For example, when two electrodes 604*a*, 604*b* are used, they may be located on either side of a printed scaffold, and an electrical current may be passed between them which creates an electrical field within the scaffold that may stimulate the cells and promote their growth and differentiation. The use of two electrodes 604*a*, 604*b* ensures that the electrical current flows through the scaffold and the cells within it, creating a circuit similar to the one used in TENS therapy. By varying the intensity and frequency of the electrical stimulation, the conditions for cell growth and tissue regeneration may be researched and optimized.

Electrical stimulation may also be used to enhance the maturation of cardiac tissue constructs, resulting in improved contractility and alignment of the cells. Additionally, electrical stimulation has been used to promote the growth of nerve cells within 3D printed scaffolds. Electrical stimulation may also be used in microfluidic systems to control the movement of cells and particles within channels. For example, electrical stimulation may be used to sort cells based on their electrical properties, such as size or surface charge. Additionally, electrical stimulation may be used to manipulate the movement of particles within microfluidic systems, such as to control the assembly of nanoparticles into specific structures.

Another difference is that the adjustable platform 600 also includes two fans 28*a* and 28*b* rather than a single fan 28 as in the case of the adjustable platform 10. The two fans 26*a* and 26*b* are connected to heat sinks 26*a* and 27*b* (e.g., see FIG. 6C) and can provide a greater amount of cooling than can be provided by fan 28 which allows the adjustable platform 600.

EXAMPLES

Example 1: Application of Electromagnetic Stimulation Via Electromagnetic Field Inductive Coupling to a 3D Bio-Printed Specimen and 3D Cell Culture Inductive coupling involves the use of a controllable EM field generated by a conductive coil that is located such that the EM field is placed around the 3D cell culture system. This EM field may be pulsed to provide pulsed EM field stimulation (PEMF) which may be is used to mimic the transmission of natural potentials in the human body. In this example, the EM stimulator is actuated with a variable magnetic field that can be applied using one EM coil or the actuation is with several variable magnetic files that can be applied using several EM coils. The intensity and frequency of levels of electromagnetic field stimulation and the conditions of cell culture may be precisely controlled. This EM stimuli has been found to modify various characteristics of adult human stem cells within 3D cell cultures for bioprinted specimens such as cell proliferation, cell cycle, and/or cell differentiation.

Example 2: Application of Mechanical Stimulation to a 3D Bio-Printed Specimen and 3D Cell Culture Mechanical stimulation with a piezoelectric transducer can be provided in a repetitive fashion with small magnitudes such that the mechanical stimulation interacts with features of printed biomaterials at the nanoscale. For example, mechanical vibration can affect cells grown on bio-printed nano-topographic patterns. As another example, mechanical vibration having an amplitude in the range of about 100 nm to about 700 nm may be used to change adhesion and gene expression. Accordingly, mechanical stimuli may be used to affect features in printed biomaterials including cell adhesion, cell cycle duration, cell shape, cytoskeletal assembly, and gene expression. A study has also recently shown that nanoscale low-frequency vibrations will lead to changes in the expression of gene products and differentiation in human mesenchymal stem cells (Marycz et al.).

In another example, mechanical stimuli may be applied such that nanometric movements of a substrate on which endothelial cells are grown may be driven by periodic sinusoidal vibration from about 1 Hz to about 50 Hz by using piezoelectric transducers. These movements in the z (vertical) axis ranges from about 5 nm to about 50 nm and are similar in vertical extent to protrusions from the cells themselves, as previously reported in the literature (e.g., Dalby et al.). Vibrational sweeps, if suitably confined within a narrow frequency range, produce similar stimulatory effects but not at wider sweeps. For example, frequencies in the range of 1 Hz to 100 Hz are generally used for mechanical stimulation of cells, but narrower range within this spectrum may be effective for producing coherent vibration and the use of a 1 or 2 Hz signal suggests that low-frequency stimulation may be effective for inducing cellular responses. These effects suggest that coherent vibration may be used for driving these cellular responses. In another example, low-intensity low frequency stimulation (e.g., applying a 5 V pk-to-pk signal at 1 or 2 Hz to a piezoelectric transducer) leads to the KLF expression.

Example 3: Application of Thermal Stimulation to a 3D Bioprinted Specimen and 3D Cell Culture Thermal stimuli that are repeatedly applied to cells in 3D printed biomaterial can induce the cells to differentiate into neuron-like cells with elongated neurites by affecting neurotrophic factors. In another example, thermal stimuli may be provided at different temperatures to affect cell proliferation and cell differentiation in different ways. In another example, thermal stimulation for bioprinted materials may be precisely programmed for use in therapeutic and regenerative medicine. Therefore, thermal stimulation may be applied to culturing cells. In addition, the bioink temperature strongly depends on the cooling rate, while isolation temperatures are independent of the heat transfer rate.

Example 4: Placement of Petri Dishes or Culture Dishes on the Bioprinter Smart Platform 4D bioprinting can be performed using a bioprinter smart platform, as described herein, for growing 3D cell cultures and bio-printed specimens in Petri dishes, cell culture plates, or other bio plates. Experiments using one or more of the stimuli provided by the bioprinter smart platform may be performed for various types of bio-printed specimens including scaffolds, organs, tissues, and other bio-printed specimens that are printed on petri dishes or other plates.

Example 5: Application of Electromagnetic Stimulation Via Electromagnetic Field Inductive Coupling to a 3D Bio-Printed Biomaterial Inductive coupling involves the use of a controllable EM field generated by a conductive coil that is located such that the EM field is placed around the 3D cell culture containing tutor and normal cells. This EM field may be pulsed to provide pulsed EM field stimulation (PEMF) which may be is used to mimic the transmission of natural potentials in the human body. In this example, the EM stimulator is actuated with a variable magnetic field that can be applied using one or more electromagnetic coils. The intensity and frequency of levels of electromagnetic field stimulation and the conditions of cell culture may be precisely controlled. This EM stimuli has been found to modify various characteristics of magnetic nanoparticles (mNPs) inside bioink and an alternating magnetic field (AMF) may be used to provide targeted heating of tumor cells.

Example 6: Application of Physical Stimulation Via Physical Coupling to a Bio Printed Dental or Orthopedic Implant and Scaffolds with or without Cells Physical stimulation applied to bioink materials demonstrates an ability to obtain a temporarily programed shape and to recover the original shape upon exposure of the material to external stimuli. Smart bed stimulation such as thermal, vibration, electrical and/or electromagnetic fields may be used for enhancing or attaining some bioink properties. The integration of Shape Memory Polymers (SMPs) in bioprinted composite may provide improved properties such as good surface enhancement, good aesthetic appeal, comfort, controlled drug release, more complicated designs (e.g., more intricate and complex structures with precise control over the placement of cells and biomaterials), hydrophilic surface properties and protection against extreme variations in environmental conditions. Several types of SMPs have been investigated for use in 3D bioprinting, including thermo-responsive SMPs, photo-responsive SMPs, and electro-active SMPs. Thermo-responsive SMPs, which can be triggered by changes in temperature, are the most commonly used for bioink applications.

In an aspect, in accordance with the teachings herein, there is provided in at least one embodiment an adjustable platform for a bioprinter, wherein the adjustable platform comprises: a housing having an upper surface with a support region for providing support for 4D printing of a biomaterial; and at least one stimulator that is mounted within the housing, the at least one stimulator being configured to provide one or more stimuli to the biomaterial during printing and/or after printing for effecting a change in structure, morphology and/or characteristic of the biomaterial, wherein the at least one stimulator comprises a mechanical stimulator, an electromagnetic stimulator, a thermal stimulator, an electric stimulator or any operable combination thereof.

In an aspect, in accordance with the teachings herein, there is provided in at least one embodiment a smart platform bed system comprising a mechanical structure on which one or more petri dishes or culture dishes can be placed during use. The smart platform bed includes one or more modular stimulators that may be located under the bioprinting bed's plate including a controllable magnetic field stimulator, a piezoelectric stimulator and/or an adjustable thermal stimulator which can generate one or more physical stimuli that may be applied to 3D bio-printed specimens, scaffolds, tissues, or organs on the petri or culture dishes for modifying their shape, morphology and/or characteristics or performing experiments under several conditions. For electromagnetic stimulation, two or more electromagnetic coils may be used.

In at least one embodiment, one or more stimuli may be applied during and/or after the bioprinting process on the bioprinter smart bed.

In at least one embodiment, one or more printed biomaterial samples are printed within an enclosed bioprinting chamber and coupled to the physical stimulator through a conductive base plate of the smart bed.

In at least one embodiment, the physical stimuli can be applied separately or simultaneously as a hybrid actuation system.

In at least one embodiment, the physical stimuli may be controlled to induce changes in cell proliferation, cell differentiation or to aid in tissue repair for 3D bioprinted specimens on the smart bed.

In at least one embodiment, the physical stimuli include electromagnetic, mechanical, electrical and/or thermal stimuli that affect bio-printed specimens.

In at least one embodiment, the electromagnetic stimuli include static or oscillating magnetic fields that have a controllable variable frequency, intensity, and time duration.

In at least one embodiment, a direct current is induced by the electromagnetic stimuli that may be used to affect the physiological properties of different cell populations in the printed biomaterial.

In at least one embodiment, a direct current or alternating current may be applied via one or more electrical contacts to the biomaterial during and/or after printing.

In at least one embodiment, the physical stimuli are selected to provide genomic effects on oligodendrocyte differentiation for the bio-printed specimen with neurotrophic factors as well as 3D cell cultures, 3D scaffolds, tissues, or organs. For example, genomic effects of magnetic fields are classified into three categories based on: (1) time-varying magnetic fields, (2) DC or static magnetic fields, and (3) application of both static fields and other energy such as thermal energy, mechanical energy, etc.

In at least one embodiment, mechanical stimuli are applied to accelerate the maturation of scaffolds maturation within a 3D cell culture. The mechanical stimuli may be provided by piezoelectric or other ultrasound transducers. The mechanical stimuli may be configured to provide cyclic strain. The mechanical stimuli have frequency, amplitude, and duration that are all controllable.

In at least one embodiment, the mechanical stimuli are applied to affect the bio-printed specimen by applying a repeatable tensile strain as well as cyclic compressive strain. Cyclic tension activates the Cbfa1/MMP-13 pathway and increases the expression of terminal differentiation hypertrophic markers. For example, evaluation of cells by time-course image analysis revealed that vibrations can enhance cell growth as an early effect but can negatively affect cell adhesion and growth profile after several passages as a delayed effect (e.g., see Kanie et al.).

In at least one embodiment, the mechanical stimuli include variable oscillating or continuous-wave ultrasound that stimulates the formation and differentiation of 3D bio-printed cells For example, cyclic tension activates the Cbfa1/MMP-13 pathway and increases the expression of terminal differentiation hypertrophic markers (e.g., see Kanie et al.).

In at least one embodiment, the mechanical stimuli may be provided by an ultrasound transducer at an intensity level of between about 1 $mW/cm^2$ and about 100 $mW/cm^2$.

In at least one embodiment, mechanical stimuli are applied to induce cyclic strain in the printed biomaterial and ultrasound is also applied. The mechanical stimulator may be operated at a frequency of about 1.0 Hz and 10% strain for cyclic strain and the ultrasound stimuli may be at about 1.0 MHz and have an intensity of about 30 $mW/cm^2$.

In at least one embodiment, the mechanical stimuli are configured to cause changes in mRNA levels to prevent atherosclerosis in 3D bio-printed cell culturing (e.g., see Zhang et al.).

In at least one embodiment, the thermal stimuli may be variable in amplitude and/or duration.

In at least one embodiment, the thermal stimuli are applied in a temperature-controlled heating or cooling step so as to cause cross-linking in a bioink structure on the smart bed (e.g., see Jin et al.).

In at least one embodiment, the thermal stimulation is applied to homogeneously proliferated 3D bio-printed scaffolds containing any type of cells.

In at least one embodiment, the thermal stimulation is configured to regulate gene expression, cell survival and cell proliferation (e.g., see Voolstra et al.).

In at least one embodiment, the smart bed platform has a flat surface region for stable placement of any Petri dishes, Falcon Cell Culture Dishes, cell culture plate, etc.

In at least one embodiment, at least one processor of the bioprinter is coupled to the stimulators of the smart bed, and the memory of the bioprinter comprises software instructions for controlling the operation of all of the stimulators and the software instructions are executed by the at least one processor.

In at least one embodiment, the bioprinter processor is configured for adjusting input parameters for mechanical stimulation, thermal stimulations, and electromagnetic stimulation.

In at least one embodiment, values for the input parameters are received from a remote software application running on a remote device operated by a user or from the bioprinter's touchscreen.

In one aspect, in accordance with the teachings herein, there is provided in at least one embodiment a method which uses a smart adjustable bed to implement 4D printing in which a magnetic field that is applied to bioprinted specimens on the smart bed's plate may be changed to provide various functions for the bio-printed specimens, including 3D cell patterning, tissue engineering, concentrating particles, translating cells, stimulating 3D cell culturing, and/or 3D cell analysis.

In at least one embodiment, the method includes providing electromagnetic stimulation using one or more electric coils.

In at least one embodiment, the method involves coupling the electromagnetic stimulation via a plate to the 3D bioprinted specimens.

In at least one embodiment, the method involves providing electromagnetic stimulation using 2 parallel electromagnetic solenoids.

In at least one embodiment, the method involves applying electromagnetic stimulation to magnetic nanoparticles in bioink for developing bio-aligned arrays.

In at least one embodiment, the method involves using with smart control of mechanical, thermal, and electromagnetic stimulation including combination thereof for providing greater superposition (hybrid) effects for cell migration and proliferation.

In at least one embodiment, the method involves applying the various stimuli provided by the smart bed individually or in any combination to perform cross-linking of polymer, hydrogel, or bioink chains during and/or after printing of one or more printed biomaterials.

In at least one embodiment, the various stimuli provided by the smart bed can be used individually or in any combination in different applications such as drug discovery, tissue engineering, life sciences, and biomedical fields such as bone, cartilage, nerve, heart, or muscle tissue engineering.

In at least one embodiment, the various stimuli provided by the smart bed can be used individually or in any combination for testing the real-world dynamic nature of tissue or organs for in-vivo applications and implants similar to implantation inside the real body (i.e., a person or animal's body).

In at least one embodiment, the various stimuli provided by the smart bed can be used individually or in any combination for obtaining a smart biomaterial response and changing morphological shape, post-printing surface treatment and changes, and more traction force for better mechanical properties.

The embodiments of the present disclosure described above are intended to be examples only and it is not intended that the applicant's teachings be limited to such embodiments. The present disclosure may be embodied in other specific forms. Alterations, modifications, and variations to the disclosure may be made without departing from the intended scope of the present disclosure. While the systems, devices, and processes disclosed and shown herein may comprise a specific number of elements/components, the systems, devices, and assemblies may be modified to include additional or fewer of such elements/components. For example, while any of the elements/components disclosed may be referenced as being singular, the embodiments disclosed herein may be modified to include a plurality of such elements/components. Selected features from one or more of the example embodiments described herein in accordance with the teachings herein may be combined to create alternative embodiments that are not explicitly described. All values and sub-ranges within disclosed ranges are also disclosed. The subject matter described herein intends to cover and embrace all suitable changes in technology. The entire disclosures of all references recited above are incorporated herein by reference.

REFERENCES

1. Bertsch S., Csontos K., Schweizer J., Marks F. Effect of mechanical stimulation on cell proliferation in mouse epidermis and on growth regulation by endogenous factors (chalones), Cell Proliferation, 1976; 9: 445-457. DOI: 10.1111/j.1365-2184.1976.tb01295.x.
2. Dalby, M. J., Manus, Biggs M. J. P., Gadegaard, N., Kalna, G., Wilkinson, C. D. W., Curtis, A. S. G., "Nanotopographical stimulation of mechanotransduction and changes in interphase centromere positioning", J Cell Biochem., 2007 Feb. 1; 100(2):326-38. doi: 10.1002/jcb.21058.
3. Fajaroh F., Setyawan H., Widiyastuti W., Winardi S. Synthesis of magnetite nanoparticles by surfactant-free electrochemical method in an aqueous system. Adv. Powder Technol. 2012; 23:328-333. DOI: 10.1016/j.apt.2011.04.007.
4. Jaatinen L, Young E, Hyttinen J, Vörös J, Zambelli T, Demkó L. Quantifying the effect of electric current on cell adhesion studied by single-cell force spectroscopy. Biointerphases. 2016; 11(1):011004. DOI: 10.1116/1.4940214.
5. Jin, X., Li, L., Xu, R., Liu, Q., Ding, L., Pan, Y., Wang, C., Hung, W., Lee, K., Wang, T., "Effects of Thermal Cross-Linking on the Structure and Property of Asymmetric Membrane Prepared from the Polyacrylonitrile", Polymers (Basel), 2018, May; 10(5): 539. DOI: 10.3390/polym10050539.
6. Kanie, K., Sakai, T., Imai, Y., Yoshida, K., Sugimoto, A., Makino, H., Kubo, H., and K. Ryuji, "Effect of mechanical vibration stress in cell culture on human induced pluripotent stem cells", Regenerative Therapy, Vol. 12, Dec. 15, 2019, Pgs. 27-35. DOI.org/10.1016/j.reth.2019.05.002.
7. Marycz K., Lewandowski D., Tomaszewski K. A., Henry B. M., Golec E. B., Marędziak M., "Low-frequency, low-magnitude vibrations (LFLM) enhances chondrogenic differentiation potential of human adipose derived mesenchymal stromal stem cells (hASCs)", PeerJ., 2016; 4: e1637. DOI: 10.7717/peerj.1637.
8. Nithin K. S., Sachhidananda S., Shilpa K. N., Sandeep S., Karthik C. S., Jagajeevan Raj B. M., Siddaramaiah H. Polymer-based smart composites and/or nanocomposites for optical, optoelectronic, and energy applications: A brief introduction, Editor(s): Nithin Kundachira Subramani, H. Siddaramaiah, Joong Hee Lee, Polymer-Based Advanced Functional Composites for Optoelectronic and Energy Applications, Elsevier, 2021, Pages 1-29.
9. Voolstra, C, Schnetzer, J., Peshkin, L., Randall, C. J., Szmant, A. M., "Effects of temperature on gene expression in embryos of the coral *Montastraea* faveolate", BMC Genomics 10, 2009; 10: 627. DOI.org/10.1186/1471-2164-10-627.
10. Wang, X., Chen, Y., Huang, C., Wang, X., Zhao, L., Zhang X., Tang, J. Contribution of a 300 kHz alternating magnetic field on magnetic hyperthermia treatment of HepG2 cells, Bioelectromagnetics, 2013; 34(2): 95-103. DOI:10.1002/bem.21761.
11. Yonggang, L. V. Application of Physical Stimulation in Stem Cell-based Tissue Engineering, Curr Stem Cell Res Ther., 2020; 15(5): 389-390. DOI: 10.2174/1574888X1505200602093146.
12. Zhang, R., Wan, J., Wang, H J., "Mechanical strain triggers differentiation of dental mesenchymal stem cells by activating osteogenesis-specific biomarkers expression", Am J Transl Res., 2019; 11(1): 233-244. PMC6357315; PMID: 30787982.
13. Zicheng, L., Gongke, L., Yuling, H., Stimuli-Responsive Polymers in Biomedical Applications, Progress in Chemistry, 2017; 29(12): 1480-1487. DOI: 10.7536/PC170703.

The invention claimed is:

1. An adjustable platform for a bioprinter, wherein the adjustable platform comprises:

a housing having an upper surface with a support region having a base plate at an upper printing surface thereof for receiving biomaterial, the base plate being conductive to transmit one or more stimuli to the biomaterial for 4D printing of the biomaterial;

at least one stimulator that is mounted within the housing and coupled to the base plate, the at least one stimulator being configured to provide one or more stimuli to the biomaterial during printing and/or after printing for effecting a change in characteristic of the biomaterial including structure and/or morphology, wherein the at least one stimulator comprises a mechanical stimulator and an electromagnetic (EM) stimulator;

wherein the EM stimulator comprises a plurality of sets of electromagnetic coils comprising a first set of electromagnetic coils arranged to generate first EM fields in the XY plane and a second set of electromagnetic coils arranged to generate second EM fields in the Z plane;

wherein the EM stimulator is configured to cause the first EM fields and the second EM fields to have a frequency of about 200 kHz to about 1 MHz; and a thermal stimulator comprising at least one thermoelectric cell that is located under the base plate and is electrically coupled to a thermal controller for receiving a control signal therefrom to generate one or more thermal stimuli with a controllable amplitude and duration.

2. The platform of claim 1, wherein the mechanical stimulator comprises at least one piezoelectric transducer that is located underneath the base plate and is electrically coupled to a mechanical controller for receiving a control signal therefrom to generate one or more mechanical stimuli with a controllable amplitude, frequency, and/or duration, the one or more mechanical stimuli being transmitted to the biomaterial during and/or after printing of the biomaterial.

3. The platform of claim 1, wherein the plurality of sets of EM coils comprises at least one electromagnetic coil that is laterally offset from a center of the base plate and is electrically coupled to an EM controller for receiving a control signal therefrom to generate one or more electromagnetic stimuli with a controllable amplitude, frequency and/or duration, the one or more electromagnetic stimuli being transmitted to the biomaterial during and/or after printing of the biomaterial.

4. The platform of claim 3, wherein the plurality of sets of EM coils comprises two or more electromagnetics coils that are spaced apart from one another and at and opposite sides of the base plate to provide different electromagnetic stimuli to different regions of the support region of the platform.

5. The platform of claim 1, wherein the thermal stimulator comprises two thermoelectric cells that are spaced apart from one another to provide different thermal stimuli to different regions of the base plate.

6. The platform of claim 1, wherein the thermal stimulator also comprises a heat sink and/or a fan that are thermally coupled to the support region of the platform for conducting heat away from the support region or conducting heat towards the support region during use depending on a temperature differential between a temperature at the support region and another temperature at the heat sink.

7. The platform of claim 1, wherein the platform further comprises at least one electrical stimulator that comprises an electrode for providing an electrical stimulus to the biomaterial.

8. A bioprinter system for 4D printing of biomaterials, wherein the bioprinter system comprises:

a housing;

a frame mounted to the housing defining an incubator chamber;

a printing head that is movably coupled to the frame for printing the biomaterials; and an adjustable platform that is moveably coupled to the frame, wherein the adjustable platform is defined according to claim 1.

9. The bioprinter system of claim 8, wherein the frame comprises at least one guide rail and a lead screw and the adjustable platform is moveably coupled to the at least one guide rail via a slide bushing and the adjustable platform is moveably coupled to the lead screw via a worm gear sleeve.

10. A method for 4D printing of biomaterial structures, wherein the method comprises:

3D printing one or more biomaterial structures; and applying at least one stimulus to the one or more biomaterial structures during and/or after bioprinting using an adjustable platform that is defined according to claim 1, wherein the at least one stimulus comprises one or more mechanical stimuli from the mechanical stimulator and/or one or more electromagnetic stimuli from the electromagnetic (EM) stimulator that are generated from within the adjustable platform.

11. The method of claim 10, wherein the method further comprises applying one or more electrical stimuli from an electrode to the one or more biomaterial structures during and/or after printing.

12. The method of claim 11, wherein the method further comprises applying one or more thermal stimuli from the thermal stimulator to the one or more biomaterial structures during and/or after printing to provide a temperature-controlled heating or cooling step.

13. The method of claim 12, wherein the method comprises controlling the amplitude, frequency, and/or duration, of the one or more stimuli to affect shape, morphology and/or at least one characteristic of the one or more printed biomaterial structures.

14. The method of claim 13, wherein the method comprises applying the one or more mechanical stimuli, the one or more electromagnetic stimuli, the one or more thermal stimuli and the one or more electrical stimuli separately or applying any combination of the one or more mechanical stimuli, the one or more electromagnetic stimuli, the one or more thermal stimuli, and the one or more electrical stimuli simultaneously.

15. The method of claim 10, wherein the one or more electromagnetic stimuli include static or oscillating magnetic fields.

16. The method of claim 10, wherein the one or more electromagnetic stimuli are applied for developing bio-aligned arrays when magnetic nanoparticles are in bioink used to print the one or more biomaterial structures.

17. The method of claim 10, wherein the one or more mechanical stimuli are applied to provide surface treatment to the one or more printed biomaterial structures.

18. The method of claim 10, wherein the one or more stimuli is applied to perform crosslinking of polymer, hydrogel, or bioink chains used to print the one or more biomaterial structures.

* * * * *